(12) United States Patent
Ross et al.

(10) Patent No.: US 12,278,042 B2
(45) Date of Patent: Apr. 15, 2025

(54) ELECTRICAL POWER TRANSFORMATION SYSTEM AND PROCESS

(71) Applicant: IONATE LIMITED, Edinburgh (GB)

(72) Inventors: Craig Ross, Edinburgh (GB); Emilia Apostol, Edinburgh (GB); Matthew Williams, Edinburgh (GB)

(73) Assignee: IONATE LIMITED, Edinburgh (GB)

( * ) Notice: Subject to any disclaimer, the term of this patent is extended or adjusted under 35 U.S.C. 154(b) by 624 days.

(21) Appl. No.: 17/642,469

(22) PCT Filed: Sep. 11, 2020

(86) PCT No.: PCT/EP2020/075470
§ 371 (c)(1),
(2) Date: Mar. 11, 2022

(87) PCT Pub. No.: WO2021/048352
PCT Pub. Date: Mar. 18, 2021

(65) Prior Publication Data
US 2022/0301767 A1 Sep. 22, 2022

(30) Foreign Application Priority Data

Sep. 13, 2019 (GB) .................................... 1913246
Oct. 28, 2019 (GB) .................................... 1915594

(51) Int. Cl.
*H01F 30/12* (2006.01)
*H01F 27/26* (2006.01)
(Continued)

(52) U.S. Cl.
CPC ............ *H01F 30/12* (2013.01); *H01F 27/26* (2013.01); *H01F 27/385* (2013.01); *H01F 30/10* (2013.01)

(58) Field of Classification Search
CPC ........ H01F 30/12; H01F 27/26; H01F 27/385; H01F 30/10; H01F 3/12; H01F 27/263;
(Continued)

(56) References Cited

U.S. PATENT DOCUMENTS 1,376,978 A * 5/1921 Stoekle ................. H01F 29/146
336/215
3,617,858 A 11/1971 Oder
(Continued)

FOREIGN PATENT DOCUMENTS

| FR | 857947 | 10/1940 |
| WO | WO 2005/027155 | 3/2005 |
| WO | WO 2017/008833 | 1/2017 |

OTHER PUBLICATIONS

Search Report & Written Opinion issued in Int'l Appl. No. PCT/EP2020/075470 (2020).

*Primary Examiner* — Tuyen T Nguyen
(74) *Attorney, Agent, or Firm* — Barnes & Thornburg LLP

(57) ABSTRACT

A transformer apparatus for an electrical power transformation system is provided. The transformer apparatus comprises three outer transformer limbs, an inner transformer limb a transfer star, and first and second connection portions. The transfer star comprises an electromagnetic transfer core and three transfer coils. The electromagnetic transfer core extends from the inner transformer limb to each of the three outer transformer limbs at a point on each outer transformer limb between the first coil assembly and the second coil assembly. The transfer coils are wound around the electromagnetic transfer core such that each transfer coil is arranged between the inner transformer limb and a respective outer transformer limb. The transfer star is configured to allow transfer of magnetomotive force between the outer transformer limbs and the inner transformer limb of the (Continued)

transformer apparatus. First and second connecting portions are to allow magnetic flux to flow between the inner and outer transformer limbs.

19 Claims, 30 Drawing Sheets

(51) Int. Cl.
*H01F 27/38* (2006.01)
*H01F 30/10* (2006.01)

(58) Field of Classification Search
CPC .. H01F 2029/143; H01F 29/146; H02M 1/12; H02M 1/4208; H02M 5/18; Y02B 70/10
See application file for complete search history.

(56) References Cited

U.S. PATENT DOCUMENTS

| | | | |
|---|---|---|---|
| 4,206,434 A * | 6/1980 | Hase | ................ H01F 21/08 336/215 |
| 2018/0218826 A1 | 8/2018 | Millsap | |

* cited by examiner

ELECTRICAL POWER TRANSFORMATION SYSTEM AND PROCESS

CROSS REFERENCE TO RELATED APPLICATIONS

This application is a U.S. nationalization under 35 U.S.C. § 371 of International Application No. PCT/EP2020/075470, filed Sep. 11, 2020, which claims priority to United Kingdom Patent Application No. 1913246.3, filed Sep. 13, 2019, and United Kingdom Patent Application No. 1915594.4, filed Oct. 28, 2019. The disclosures set forth in the referenced applications are incorporated herein by reference in their entireties.

TECHNICAL FIELD

The present invention relates to electrical energy supply, and in particular to an electrical power transformation system and process.

BACKGROUND

Electrical energy is delivered from its generation source to the load that consumes it via wires. The electricity is generally transferred at higher voltages than is safe for use as this provides much better efficiency during the transportation. Transformers are used within an electricity system to transform the voltage of electricity via a fixed ratio, either increasing or decreasing the voltage level. Transformers were first invented more than 100 years ago and have not significantly evolved.

As electricity requirements change the existing infrastructure such as transformer are not enough to maintain a reliable energy system. Traditionally the electricity has been generated by a small number of large synchronous generators, providing both the power and stability for the system. The increase of asynchronous variable renewable generation within the electricity system is having adverse effects on its operational stability. The lack of inertia within the system as traditional synchronous fossil fuel generation is lost, coupled with the change from a small number of large generators to large quantities of distributed generators throughout the system has increased the fragility of the network as well as increased energy prices.

Additional equipment must be used within the system to maintain the power quality and reliability of the electricity system. These are primarily additional expensive equipment, with more complexity and a shorter lifespan, leading to a more fragile and costly system.

It would be desirable to have a single device which was able to complete the required voltage transformation, but also provide additional features such as dynamic voltage control, harmonics suppression, and power factor control. Devices exist which provide only part of this functionality, such as described below.

Transformer

As known by those skilled in the art, a transformer is an electromagnetic device that transfers electric energy from one circuit to another circuit via mutual inductance, and is typically made up of a primary winding, a magnetic core and a secondary winding. When an alternating voltage is applied to the primary winding, an alternating current flows through the primary winding. This magnetizing current produces an alternating magnetic flux. The flux is mostly constrained within the magnetic core, and induces voltage in the linked secondary winding, which if connected to an electrical load produces an alternating current. This secondary load current then produces its own alternating magnetic flux which links back with the primary winding.

The secondary voltage is determined by the product of the primary voltage and the ratio of the number of turns in the secondary winding and the number of turns in the primary winding. Transformers are commonly used to convert between high and low voltages, but they are bulky by necessity at distribution frequencies. They offer high efficiency, simplicity of design, and bidirectional power transfer. However their passive nature affords limited regulation of the power transferred, requiring the introduction of inefficient voltage regulation assets.

Within the electricity grid voltage must be kept within strict tolerances in order for equipment to operate effectively and safely. It would be desirable to have a device which was able to dynamically and precisely control voltage, decoupling the supply and load side voltages, and allowing the correct voltage levels to be maintained.

Solid State Transformer

A solid state transformer is a replacement for an existing transformer. It consists of a number of component parts connected in series. These parts are a rectifier, an inverter, an electromagnetic core, a rectifier and an inverter. The higher voltage side is connected to the first inverter, which transforms the power from AC (generally 50 Hz or 60 Hz) to DC. The rectifier then transforms the power from DC to a much higher frequency AC waveform. This allows the electromagnetic core of the device to be considerably smaller and cheaper, whilst still providing the voltage transformation. The next rectifier transforms the high frequency AC power to DC, with the final inverter transforming the power back to 50 Hz (or 60 Hz) AC. The control of the power electronics components allows both power factor and additional voltage control to be delivered.

However, these devices are not yet a commercial product and face some challenges before being able to deliver benefits in the real world. These technology challenges include a smaller lifespan and reliability of the power electronics, as well as high costs at power levels the electricity grid operates at.

Exchanger

An Exchanger is a device for the purpose of providing voltage transformation, voltage control, power factor control, and harmonic suppression. It consists of three independent shell type single phase electromagnetic cores. Each single-phase core has a control winding connected to a back to back inverter. The inverters are controlled to provide a current through the control winding that generates an out of phase magnetic field within the electromagnetic core. Each phase of the device is controlled separately and are not connected.

However, these devices are not yet a commercial product and face some challenges before being able to deliver benefits in the real world. These technology challenges include a efficiency, weight, and cost.

Real and Reactive Power

Energy flows through AC power circuits which generally and resistive, capacitive and inductive components. To know the total power consumed, both the voltage and the current must be known, as Power equals the voltage multiplied by the current.

As the value of the voltage and current both change over time in an AC circuit, the maximum power will be when both peak at the same time. This is called the voltage and current being "in phase".

Active power is the energy consumed by the resistive load, and does useful work. Reactive power is the power consumed that does no useful work. This is created by the fact that the energy stored by a capacitors electrostatic field tries to control the voltage, whilst the energy stored by an inductor in its magnetic field tries to control the current. The result is that capacitors "generate" reactive power and inductors "consume" reactive power. This means that they both consume and return power to the source so none of the real power is consumed. The apparent power of the of system is the vector sum of the active and reactive power components, which are at 90 degrees to each other.

Power Factor is a term used to describe the ratio between the active power and apparent power. When the power factor is 1, real and apparent power are equal, hence reactive power must be zero. When the power factor is less than 1, energy is being used for non-useful work as reactive power.

Within an electricity grid, the power factor is determined by the load on the system. If the load has a poor power factor this is propagated through the grid to the generators, leading to capacity reduction of the wires for active power and higher losses.

It would be desirable for a device to be able to control power factor, decoupling the load power factor from the supply side, therefore increasing the efficiency and capacity of the electricity system.

SUMMARY

According to a first aspect of the disclosure, a transformer apparatus for an electrical power transformation system is provided. The transformer apparatus comprises:
three outer transformer limbs, each transformer limb comprising:
  an electromagnetic core;
  a first coil assembly comprising a first primary coil and a first secondary coil, the first primary coil and the first secondary coil wound concentrically around the electromagnetic core;
  a second coil assembly comprising a second primary coil and a second secondary coil, the second primary coil and the second secondary coil wound concentrically around the electromagnetic core;
  wherein the first coil assembly and the second coil assembly are spaced apart along the electromagnetic core,
  each first primary coil is connected in series to the second primary coil of the respective transformer limb, and
  each first secondary coil is connected in series to the second secondary coil of the respective transformer limb;
an inner transformer limb comprising an electromagnetic core, wherein the outer transformer limbs are arranged about the inner transformer limb;
a transfer star comprising:
  an electromagnetic transfer core extending from the inner transformer limb to each of the three outer transformer limbs at a point on each outer transformer limb between the first coil assembly and the second coil assembly;
  three transfer coils, the transfer coils wound around the electromagnetic transfer core such that each transfer coil is arranged between the inner transformer limb and a respective outer transformer limb,
  wherein the transfer star is configured to allow transfer of magnetomotive force between the outer transformer limbs and the inner transformer limb of the transformer apparatus;
a first connecting portion provided towards a first end of each outer transformer limb and towards a first end of the inner transformer limb, the first connecting portion connecting each of the first ends of the outer transformer limbs and the first end of the inner transformer limb together and configured to allow magnetic flux to flow between each of the first ends of the inner and outer transformer limbs; and
a second connecting portion provided towards a second opposing end of each outer transformer limb and towards a second opposing end of the inner transformer limb, the second connecting portion connecting each of the second ends of the outer transformer limbs and the second end of the inner transformer limb together and configured to allow magnetic flux to flow between each of the second ends of the inner and outer transformer limbs.

In some embodiments, each first coil assembly further comprises:
  a first reaction coil wound concentrically around the electromagnetic core with the first primary coil and the first secondary coil; and
each second coil assembly further comprises:
  a second reaction coil wound concentrically around the electromagnetic core with the second primary coil and the second secondary coil.

According to a second aspect of the disclosure, a transformer apparatus for an electrical power transformation system is provided. The transformer apparatus comprises:
three outer transformer limbs, each outer transformer limb comprising:
  an electromagnetic core;
  a first coil assembly comprising a first primary coil, a first secondary coil, and a first reaction coil, the first primary coil, the first secondary coil and first reaction coil wound concentrically around the electromagnetic core;
an inner transformer limb comprising an electromagnetic core;
a first connecting portion provided towards a first end of each outer transformer limb and towards a first end of the inner transformer limb, the first connecting portion connecting each of the first ends of the outer transformer limbs and the first end of the inner transformer limb together and configured to allow magnetic flux to flow between each of the first ends of the inner and outer transformer limbs; and
a second connecting portion provided towards a second opposing end of each transformer limb and towards a second opposing end of the inner transformer limb, the second connecting portion connecting each of the second ends of the outer transformer limbs and the second end of the inner transformer limb together and configured to allow magnetic flux to flow between each of the inner and outer second ends of the transformer limbs.

In some embodiments, each outer transformer limb further comprises:
  a second coil assembly comprising a second primary coil, a second secondary coil, and a second reaction coil, the second primary coil, the second secondary coil, and the second reaction coil wound concentrically around the electromagnetic core;

wherein the first coil assembly and the second coil assembly are spaced apart along the electromagnetic core,
each first primary coil is connected in series to the second primary coil of the respective outer transformer limb, and
each first secondary coil is connected in series to the second secondary coil of the respective outer transformer limb,
the transformer apparatus further comprising:
a transfer star comprising:
an electromagnetic transfer core extending from the inner transformer limb to each of the three outer transformer limbs at a point on each outer transformer limb between the first coil assembly and the second coil assembly;
three transfer coils, the transfer coils wound around the electromagnetic transfer core such that each transfer coil is arranged between the inner transformer limb and a respective outer transformer limb,
wherein the transfer star is configured to allow transfer of magnetomotive force between the transformer limbs of the transformer apparatus.

A transformer apparatus according to the first or second aspect may also have, in some embodiments, one or more of the following features.

In some embodiments, at least one of the transfer star, the first connecting portion, and the second connecting portion comprises a stacked laminate of an electromagnetic material.

In some embodiments, for each first coil assembly, the first secondary coil is wound around the electromagnetic core, and the first primary coil is wound concentrically around the first secondary coil. In some embodiments, for each second coil assembly, the second secondary coil is wound around the electromagnetic core, and the second primary coil is wound concentrically around the second secondary coil.

In some embodiments, for each first coil assembly, the first reaction coil is wound around the electromagnetic core, and the first secondary coil is wound concentrically around the first reaction coil, and the first primary coil is wound concentrically around the first secondary coil. In some embodiments, for each second coil assembly, the second reaction coil is wound around the electromagnetic core, and the second secondary coil is wound concentrically around the second reaction coil, and the second primary coil is wound concentrically around the second secondary coil.

In some embodiments, the electromagnetic core of each outer transformer limb comprises:
a first electromagnetic core portion on which the first coil assembly is provided; and
a second electromagnetic core portion on which the second coil assembly is provided,
wherein the transfer star is provided between the first and second electromagnetic core portions of each outer transformer limb; wherein optionally the electromagnetic core of the inner transformer limb comprises:
a first electromagnetic core portion; and
a second electromagnetic core portion;
wherein the transfer star is provided between the first and second electromagnetic core portions of the inner transformer limb.

In some embodiments, each reaction coil has a variable reactance.

In some embodiments, the inner transformer limb is arranged at a geometric centre of the outer transformer limbs. In some embodiments, the outer transformer limbs are arranged about the inner transformer limb 120° apart.

According to a third aspect of the disclosure, an electrical power transformation system is provided. The electrical power transformation system is configured to receive a three phase power input and output a three phase power output having a transformed voltage. The electrical power transformation system comprises a transformer apparatus according to the first aspect of the disclosure, or in some embodiments, a transformer apparatus according to embodiments of the second aspect of the disclosure including the transfer coils. The first and second primary coils of each outer transformer limb are configured to be connected across a respective phase of the three phase power input, and the first and second secondary coils of each outer transformer limb are configured to be connected across a respective phase of the three phase power output. The electrical power transformation system also comprises a controller configured to control each of the three transfer coils in order to selectively transfer magnetomotive force between the transformer limbs of the transformer apparatus based on the three phase power input and the three phase power output.

In some embodiments of the third aspect where the transformer apparatus comprises reaction coils, the controller is further configured to:
determine a power factor of the three phase power output on the secondary coils and output a reaction signal to each reaction coil to control a reactance of the respective reaction coil in order to control a power factor of the three phase power input on the primary coils.

According to a fourth aspect of the disclosure, an electrical power transformation system is provided. The electrical power transformation system is configured to receive a three phase power input and output a three phase power output having a transformed voltage. The electrical power transformation system comprises a transformer apparatus according to the second aspect of the disclosure, or in some embodiments, a transformer apparatus according to embodiments of the first aspect of the disclosure including the reaction coils. The primary coil(s) of each outer transformer limb are configured to be connected across a respective phase of the three phase power input, and the secondary coil(s) of each outer transformer limb are configured to be connected across a respective phase of the three phase power output. The electrical power transformation system also comprises a controller configured to determine a power factor of the three phase power output and provide a reaction signal to each reaction coil to control a reactance of the respective reaction coil in order to control a power factor of the three phase power input.

In some embodiments of the fourth aspect where the transformer apparatus includes transfer coils, the controller is further configured to:
control each of the three transfer coils in order to selectively transfer magnetomotive force between the inner and outer transformer limbs of the transformer apparatus based on the three phase power input and the three phase power output An electrical power transformation system according to the third or fourth aspect may also have, in some embodiments, one or more of the following features.

In some embodiments, the electrical power transformation system further comprises:
a plurality of reaction circuits, each reaction circuit configured to control the variable reactance of a respective reaction coil in response to a respective reaction signal from the controller.

In some embodiments, the controller is configured to output a reaction signal for each reaction circuit to control the variable reactance of the respective reaction coil in order to control a power factor of the three phase power input.

In some embodiments, the controller controls each of the three transfer coils in order to selectively transfer magnetomotive force between the inner and outer transformer limbs of the transformer apparatus in order to control a ratio of voltage transformation between the primary and secondary coils of each outer transformer limb.

In some embodiments, the electrical power transformation system further comprises an inverter circuit configured to drive each of the three transfer coils in response to a control signal from the controller. In some embodiments, the inverter circuit further comprises at least one energy storage element for each of the three transfer coils configured to store energy for driving each of the three transfer coils. In some embodiments, the inverter circuit outputs a pulse width modulated signal to each of the three transfer coils.

In some embodiments, the controller is configured to control a phase of a control signal driving each transfer coil with respect to a phase of the three phase input power to control a reactive power transferred between transformer limbs of transformer apparatus.

According to a fifth aspect of the disclosure, a method of transforming three phase power is provided. The method comprises:
   inputting a three phase power input to the electrical power transformation system of the third or fourth aspect;
   transforming the three phase power input to a three phase power output, wherein a voltage and/or power factor of the three phase voltage output and/or input is controlled by the controller.

In the first and second aspects of the disclosure, it will be appreciated that the outer transformer limbs are arranged about an inner core. As such, it will be appreciated that the transformer apparatus is provided in a star configuration for the transformation of three phase power. As is known to the skilled person, three phase power may also be transformed using a delta configuration. Delta-configured three phase power systems are effectively an alternative design solution to star configured three phase power systems. Against this background, it will be appreciated that the transformer apparatus of the first through fifth aspects may also be implemented in a delta configuration. For example, a delta-configured transformer apparatus is described in this disclosure, the aspects of which are set out below.

According to a sixth aspect of the disclosure, a transformer apparatus for an electrical power transformation system is provided. The transformer apparatus comprises:
   three transformer limbs, each transformer limb comprising:
      an electromagnetic core;
      a first coil assembly comprising a first primary coil and a first secondary coil, the first primary coil and the first secondary coil wound concentrically around the electromagnetic core;
      a second coil assembly comprising a second primary coil and a second secondary coil, the second primary coil and the second secondary coil wound concentrically around the electromagnetic core;
      wherein the first coil assembly and the second coil assembly are spaced apart along the electromagnetic core,
      each first primary coil is connected in series to the second primary coil of the respective transformer limb, and
      each first secondary coil is connected in series to the second secondary coil of the respective transformer limb;
   a transfer ring comprising:
      an electromagnetic transfer core extending between each of the three transformer limbs at a point on each limb between the first coil assembly and the second coil assembly;
      three transfer coils, the transfer coils wound around the electromagnetic transfer core such that a transfer coil is arranged between each adjacent pair of transformer limbs,
      wherein the transfer ring is configured to allow transfer of magnetomotive force between the transformer limbs of the transformer apparatus;
   a first connecting portion provided towards a first end of each transformer limb, the first connecting portion connecting each of the first ends of the transformer limbs together and configured to allow magnetic flux to flow between each of the first ends of the transformer limbs; and
   a second connecting portion provided towards a second opposing end of each transformer limb, the second connecting portion connecting each of the second ends of the transformer limbs together and configured to allow magnetic flux to flow between each of the second ends of the transformer limbs.

In some embodiments, each first coil assembly further comprises:
   a first reaction coil wound concentrically around the electromagnetic core with the first primary coil and the first secondary coil; and
each second coil assembly further comprises:
   a second reaction coil wound concentrically around the electromagnetic core with the second primary coil and the second secondary coil.

According to a seventh aspect of the disclosure, a transformer apparatus for an electrical power transformation system is provided. The transformer apparatus comprises:
   three transformer limbs, each transformer limb comprising:
      an electromagnetic core;
      a first coil assembly comprising a first primary coil, a first secondary coil, and a first reaction coil, the first primary coil, the first secondary coil and first reaction coil wound concentrically around the electromagnetic core;
   a first connecting portion provided towards a first end of each transformer limb, the first connecting portion connecting each of the first ends of the transformer limbs together and configured to allow magnetic flux to flow between each of the first ends of the transformer limbs; and
   a second connecting portion provided towards a second opposing end of each transformer limb, the second connecting portion connecting each of the second ends of the transformer limbs together and configured to allow magnetic flux to flow between each of the second ends of the transformer limbs.

In some embodiments, each transformer limb further comprises:
   a second coil assembly comprising a second primary coil, a second secondary coil, and a second reaction coil, the second primary coil, the second secondary coil, and the second reaction coil wound concentrically around the electromagnetic core;

wherein the first coil assembly and the second coil assembly are spaced apart along the electromagnetic core, each first primary coil is connected in series to the second primary coil of the respective transformer limb, and each first secondary coil is connected in series to the second secondary coil of the respective transformer limb, the transformer apparatus further comprising:

a transfer ring comprising:

an electromagnetic transfer core extending between each of the three transformer limbs at a point on each limb between the first coil assembly and the second coil assembly;

three transfer coils, the transfer coils wound around the electromagnetic transfer core such that a transfer coil is arranged between each adjacent pair of transformer limbs, wherein the transfer ring is configured to allow transfer of magnetomotive force between the transformer limbs of the transformer apparatus.

In some embodiments of the sixth or seventh aspect of the disclosure the electromagnetic core of each transformer limb comprises:

a first electromagnetic core portion on which the first coil assembly is provided; and a second electromagnetic core portion on which the second coil assembly is provided, wherein transfer ring is provided between the first and second electromagnetic core portions of each transformer limb.

It will be appreciated that the transformer apparatus according to the sixth or seventh aspect may also have, in some embodiments any of the optional features of the first or second aspect as described above. Furthermore, it will be appreciated that the transformer apparatus of the sixth and seventh aspect may be used in the electrical power transformation system of the third and fourth aspects as described above. The transformer apparatus of the sixth and seventh aspects may also be used in the method of the fifth aspect.

According to an eighth aspect of the disclosure, a transformer apparatus for an electrical power transformation system is provided. The transformer apparatus comprises a first transformer limb, a second transformer limb, an electromagenetic transfer limb, a transfer coil, a first connecting portion, and a second connecting portion. The first transformer limb comprises an electromagnetic transfer core, a first coil assembly, and a second coil assembly. The first coil assembly comprises a first primary coil and a first secondary coil. The first primary coil and the first secondary coil are wound concentrically around the electromagnetic core. The second coil assembly comprises a second primary coil and a second secondary coil. The second primary coil and the second secondary coil are wound concentrically around the electromagnetic core. The first coil assembly and the second coil assembly are spaced apart along the electromagnetic core. The first primary coil is connected in series to the second primary coil of the first transformer limb, and the first secondary coil is connected in series to the second secondary coil of the first transformer limb. The second transformer limb comprises an electromagnetic transfer core. The electromagnetic transfer limb is connected to the first transformer limb and the second transformer limb at a point on the first transformer limb between the first coil assembly and the second coil assembly. The transfer coil is wound around the electromagnetic transfer limb. The electromagnetic transfer limb is configured to allow transfer of magnetomotive force between the first transformer limb and the second transformer limb of the transformer apparatus. The first connecting portion is provided towards a first end of the first transformer limb and towards a first end of the second transformer limb. The first connecting portion connects the first end of the first transformer limb and the first end of the second transformer limb together and is configured to allow magnetic flux to flow between the first ends of the first and second transformer limbs. The second connecting portion is provided towards a second opposing end of the first transformer limb and towards a second opposing end of the second transformer limb. The second connecting portion connects the second end of the first transformer limb and the second end of the second transformer limb together and configured to allow magnetic flux to flow between the second ends of the first and second transformer limbs.

In some embodiments, the first coil assembly further comprises a first reaction coil wound concentrically around the electromagnetic core with the first primary coil and the first secondary coil, and the second coil assembly further comprises a second reaction coil wound concentrically around the electromagnetic core with the second primary coil and the second secondary coil.

In some embodiments, at least one of the first or second transfer limbs, and the electromagnetic core comprises a stacked laminate of an electromagnetic material.

In some embodiments, the first secondary coil is wound around the electromagnetic core, and the first primary coil is wound concentrically around the first secondary coil. In some embodiments, the second secondary coil is wound around the electromagnetic core, and the second primary coil is wound concentrically around the second secondary coil.

In some embodiments, the first reaction coil is wound around the electromagnetic core, and the first secondary coil is wound concentrically around the first reaction coil, and the first primary coil is wound concentrically around the first secondary coil. In some embodiments, the second reaction coil is wound around the electromagnetic core, and the second secondary coil is wound concentrically around the second reaction coil, and the second primary coil is wound concentrically around the second secondary coil.

In some embodiments, the first and second reaction coils have a variable reactance.

According to a ninth aspect of the disclosure, an electrical power transformation system is provided. The electrical power transformation system is configured to receive a single phase power input and output a single phase power output having a transformed voltage. the electrical power transformation system comprises a transformer apparatus according to the eighth aspect of the disclosure, wherein the first and second primary coils of the first transformer limb are configured to be connected across a single phase of the single phase power input, and the first and second secondary coils of the first transformer limb are configured to be connected across a single phase of the single phase power output. The electrical power transformation system also comprises a controller configured to control the transfer coil in order to selectively transfer magnetomotive force between the first and second transformer limb of the transformer apparatus based on the single phase power input and the single phase power output.

In some embodiments, the controller of the transformer apparatus of the eight aspect is further configured to determine a power factor of the single phase power output on the secondary coils and output a reaction signal to each reaction coil to control a reactance of the respective reaction coil in order to control a power factor of the single phase power input on the primary coils.

In some embodiments, the electrical power transformation system further comprises a plurality of reaction circuits, each reaction circuit configured to control the variable reactance of a respective reaction coil in response to a respective reaction signal from the controller.

In some embodiments, the controller outputs a reaction signal for each reaction circuit to control the variable reactance of the respective reaction coil in order to control a power factor of the single phase power input.

In some embodiments, the controller controls the transfer coil in order to selectively transfer magnetomotive force between the first and second transformer limbs of the transformer apparatus in order to control a ratio of voltage transformation between the primary and secondary coils of the first transformer limb.

In some embodiments, the electrical power transformation system according further comprises an power electronics circuit configured to drive the transfer coil in response to a control signal from the controller. In some embodiments, the power electronics circuit further comprises at least one energy storage element for the transfer coil configured to store energy for driving the transfer coil. In some embodiments, the power electronics circuit outputs a pulse width modulated signal to the transfer coil.

In some embodiments, the controller is configured to control a phase of a control signal driving the transfer coil with respect to a phase of the single phase input power to control a reactive power transferred between the first and second transformer limbs of transformer apparatus.

According to a tenth aspect of the disclosure a method of transforming single phase power is provided. The method comprises inputting a single phase power input to the electrical power transformation system of the ninth aspect, and transforming the single phase power input to a single phase power output, wherein a voltage and/or power factor of the single phase voltage output is controlled by the controller.

It will be appreciated that the eighth, ninth and tenth aspects of the disclosure relate to a single phase implementation of the transformer apparatus disclosed in the first through seventh aspects of the disclosure. As such, any optional features or advantages associated with any of the first through seventh aspects of the disclosure may also apply to the eighth, ninth, and tenth aspects of the disclosure.

BRIEF DESCRIPTION OF THE DRAWINGS

Some embodiments of the present invention will now be described, by way of example only, with reference to the accompanying figures, wherein.

DETAILED DESCRIPTION

Embodiments of the present invention include a transformer apparatus, an electrical power transformation system and process that involve receiving three phases of input electrical energy, each having its own active and reactive power component through its voltage and phase, and converting each of these three inputs simultaneously to a desired or 'target' output voltage and phase and therefore active and reactive power components (i.e. a method of transforming three phase power).

The three inputs will vary over time in both voltage and phase, both absolutely and relative to each other, and thus the system and process operate to dynamically control the transformation of the energy through the apparatus so that the output electrical energy has the desired voltage and phase, which themselves can be varied over time.

Embodiments of the present invention are able to provide RMS voltage conversion while simultaneously providing power factor correction and harmonics suppression, through controlling energy transfer between the three phases in the magnetic domain using a electromagnetic pathway. This delivers a more efficient and cost-effective solution, as well as electrically isolating the input and output of the device.

Although embodiments of the present invention are primarily described herein in the context of power distribution within an electricity grid, it will be apparent to those skilled in the art that other embodiments may be used in any electrical system application that requires control of output voltage and or power factor, such as electrical systems for power generation, aviation, rail, marine, energy storage, and other applications, for example. Many other applications of the electrical power supply system and process described herein will be apparent to those skilled in the art in light of this disclosure.

In this specification, unless the context indicates otherwise, the term "signal" is used for convenience of reference, and is to be construed broadly as referring to a form of electrical energy characterised by a voltage and at least one fundamental frequency (which could be zero in the case of a DC voltage), and does not necessarily require that any form of information is represented by or conveyed by the signal.

Overview

Figure 8:
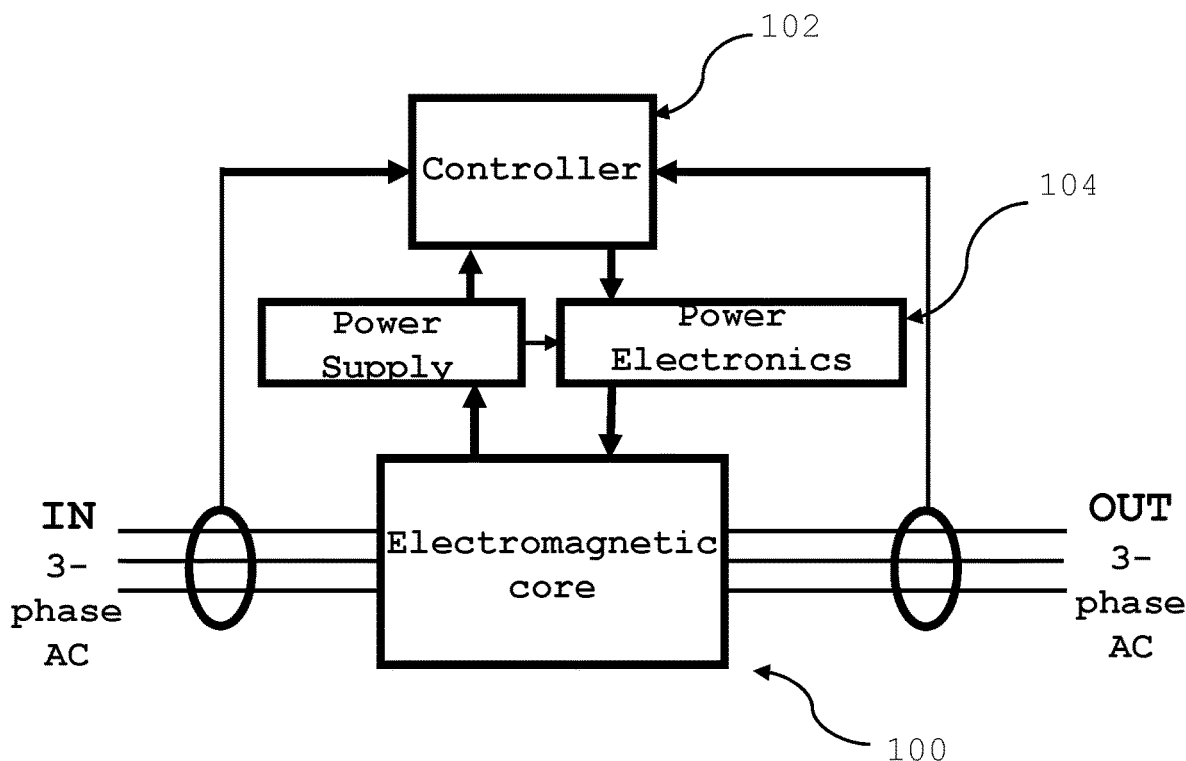
FIG. 8 is a block diagram of the component parts of an electrical energy transformation system in accordance with some embodiments of the present invention.

As shown in FIG. 8, an electrical power transformation system includes an electromagnetic core (e.g. a transformer apparatus) 100, power electronics (e.g. an inverter circuit) 104, and a controller 102. The controller 102 has input signals from monitoring the three-phase electrical input and three-phase electrical output and uses these to provide a control signal to the power electronics. The power electronics 104 control the power flowing through the transfer coils on the electromagnetic core 100. The electromagnetic core 100 is also connected to both the three-phase electrical input and three-phase electrical output, providing the voltage transformation, power factor correction, and harmonics suppression. The controller 102 and the power electronics 104 are powered by a coil on the magnetic core 100. This allows the device to be self-powered as well as conserving energy. Alternatively, the control and power electronics can be powered from an external power source, such as a battery or a mains power connection. This would remove the need for the additional coil or coils on the magnetic core, without impacting the remainder of the device.

Figure 7:
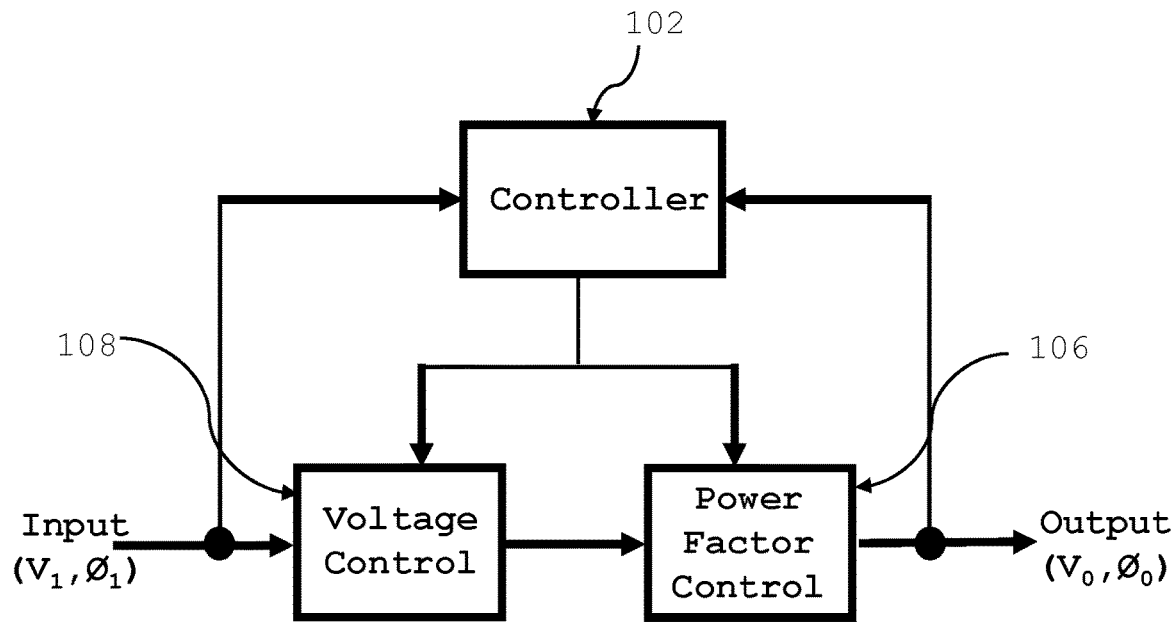
FIG. 7 is a block diagram of a single phase of an electrical energy transformation system in accordance with some embodiments of the present invention.

The device operates within a three-phase system, with each phase having both a voltage control component (108) and a power factor control component (106). As shown in FIG. 7, each phase input has a voltage and a phase angle, and each output has a voltage and a phase angle. The controller 102 monitors the input and output of this phase, as well as the other two simultaneously, and provides a control signal to the voltage control component 108 and the power factor control component 106.

Electromagnetic Core (Delta Arrangement)

Figure 1:
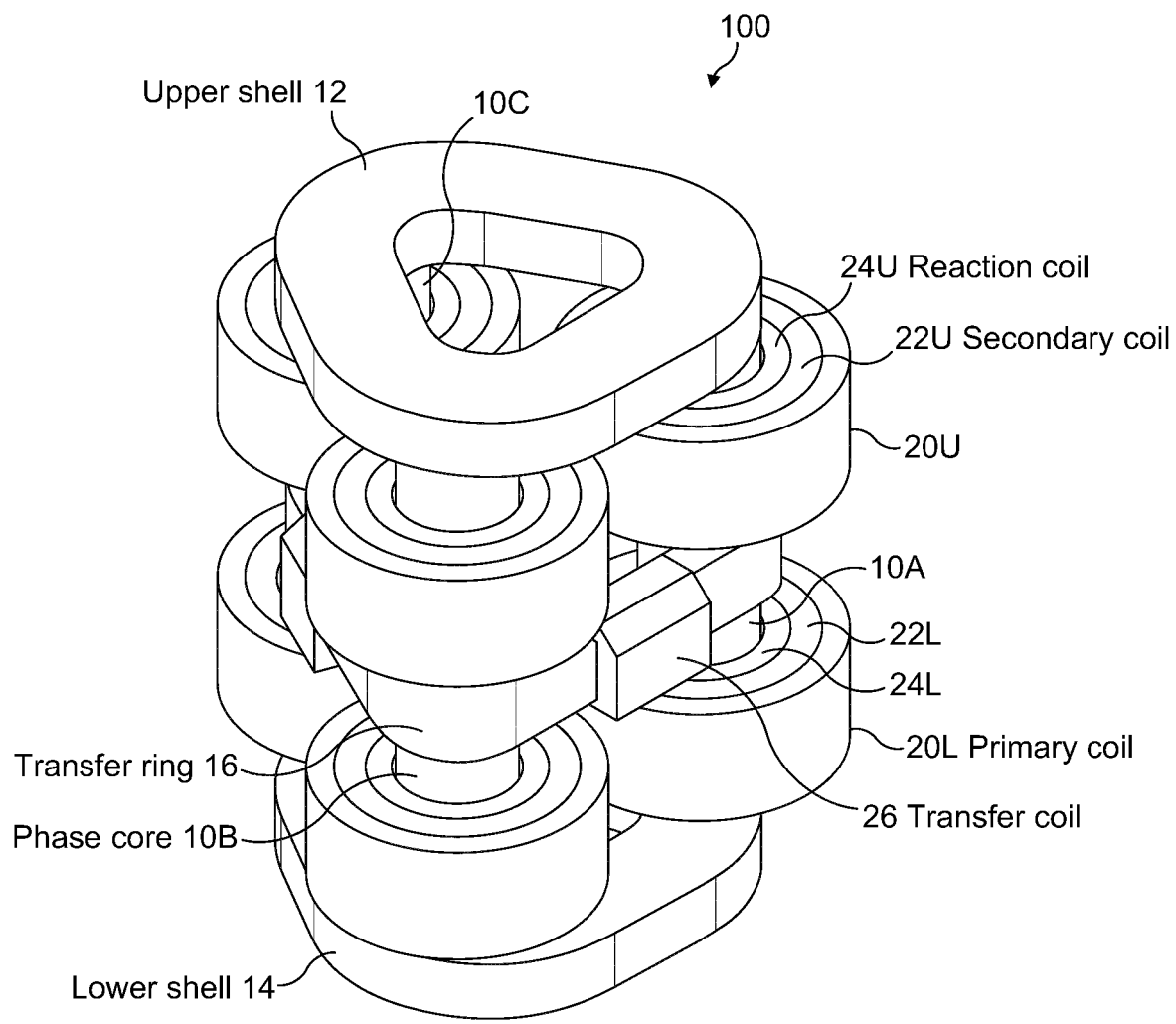
FIG. 1 is a three-dimensional diagram of the electromagnetic core and windings in accordance with some embodiments of the present invention.

The electromagnetic core (transformer apparatus) 100 of the device is shown in FIG. 1. It consists of three limbs 10A, 10B, 10C, one for each phase of the three-phase power flowing through the device (Phase A, B, and C), connected at one end by an upper shell 12, and at the other end by a lower shell 14. This provides a magnetically symmetrical core for all three phases A, B, C. The electromagnetic core 100 is in the form of a delta connection, and as such may be considered to be an electromagnetic Delta Core, or Delta Core. A transfer ring 16 is connected to each of the three limbs 10A, 10B, 10C between the upper and lower shells 12, 14, providing an additional pathway for magnetic flux to flow. The (Delta) core 100 may be made of any magnetic material whose including but not limited to ferromagnetic materials. The core itself may be formed as a unitary structure, or may be constructed from multiple component parts, which may be made from the same or different materials for different regions of the magnetic core.

Each limb 10A, 10B, 10C has two sets of concentrically wound coils, one above the transfer ring and one below. The upper coil on the phase A limb is denoted $A_u$, the lower coil on the phase A limb is denoted $A_l$. Likewise phase B and C coils are denoted $B_u$, $B_l$, $C_u$, and $C_l$. Each set of concentrically wound coils has three separate coils, a primary 20U, 20L, a secondary 22U, 22L, and a reaction coil 24U, 24L. Each pair of primary coils on a limb are connected in series. Each pair of secondary coils on a limb are connected in series. Each pair of reaction coils may be connected in series, or each reaction coil may be independently connected to control circuitry. The transfer ring has three transfer coils 26 wound on it, one between each of the limbs. These are denoted $T_{AB}$, $T_{BC}$, and $T_{AC}$. A three-dimensional single line diagram of the electromagnetic core with these labels is shown in FIG. 2.

In total there are 21 coils on the electromagnetic Delta core. These coils can be wound in different manners as would a standard transformer coils be wound. These include helical, disc, cylindrical, and crossover, as described at https://www.electrical4u.com/transformer-winding/for example.

Figure 2:
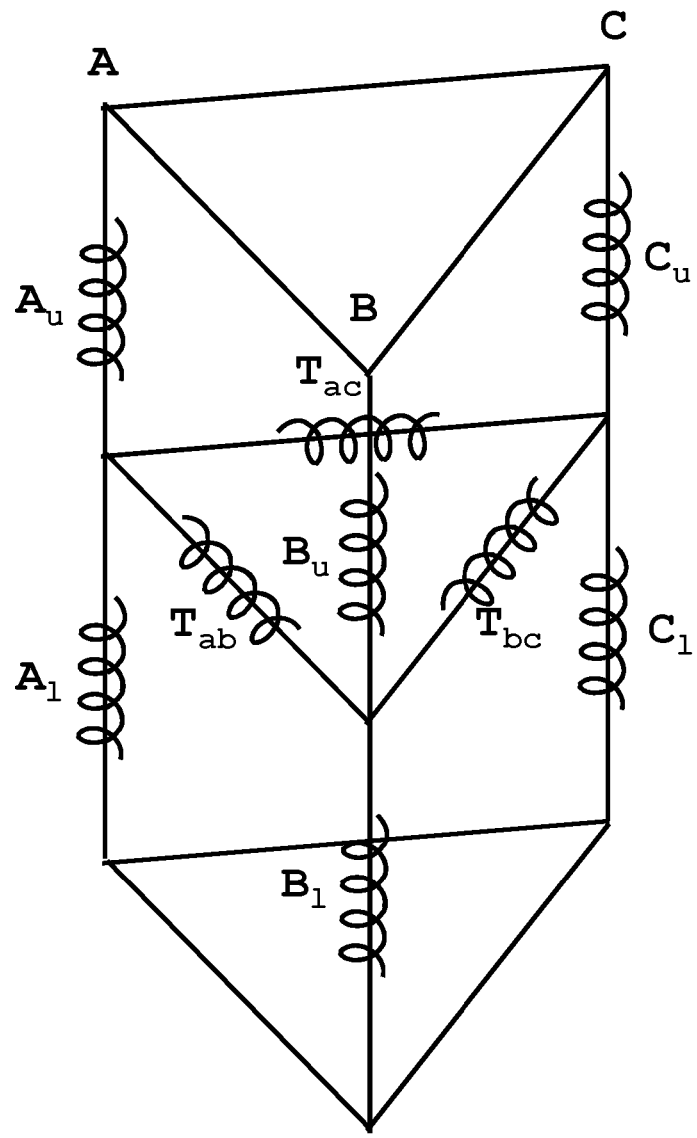
FIG. 2 is a three-dimensional single line diagram of the electromagnetic core windings in accordance with some embodiments of the present invention.
Figure 3:
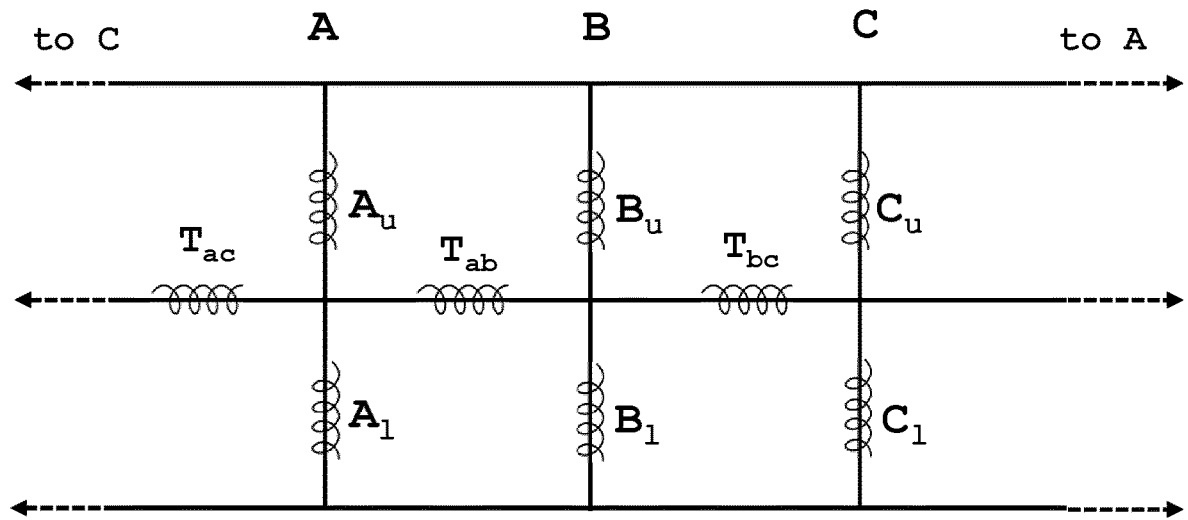
FIG. 3 is a two-dimensional single line representation of the electromagnetic core windings in accordance with some embodiments of the present invention.
Figure 4:
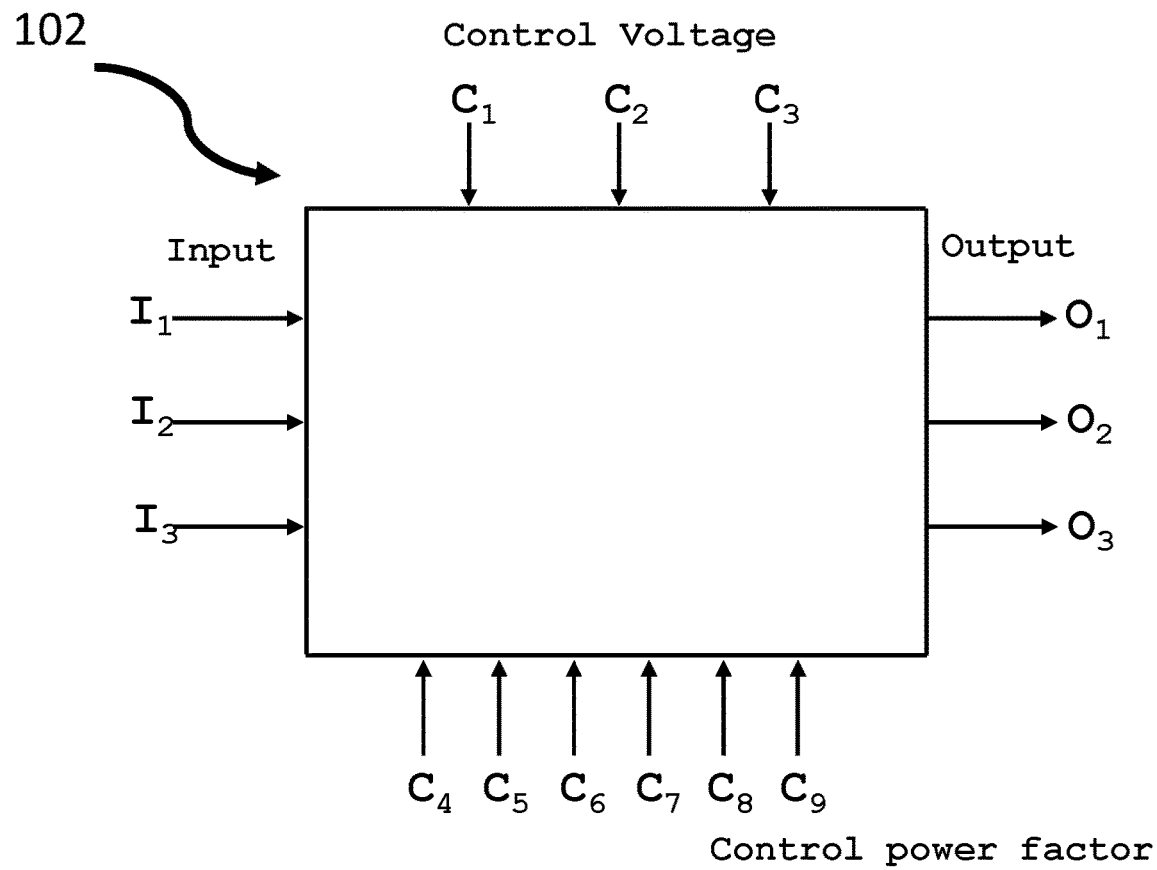
FIG. 4 is a block diagram showing the power inputs and outputs of the device, and the control inputs.
Figure 9:
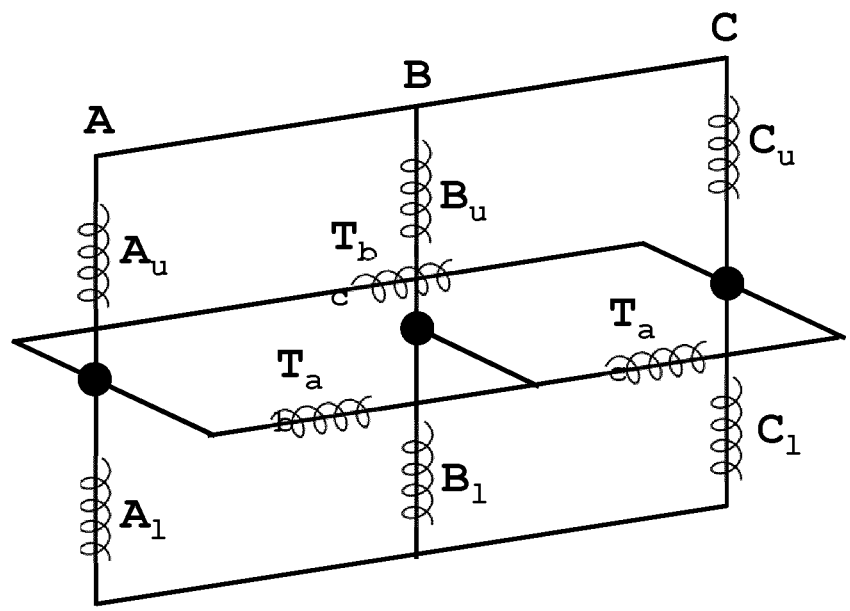
FIG. 9 is a three-dimensional single line diagram of an alternative electromagnetic core arrangement, using a standard three-phase shell type transformer, with an physical electromagnetic transfer link between each of the three phases.
Figure 14:
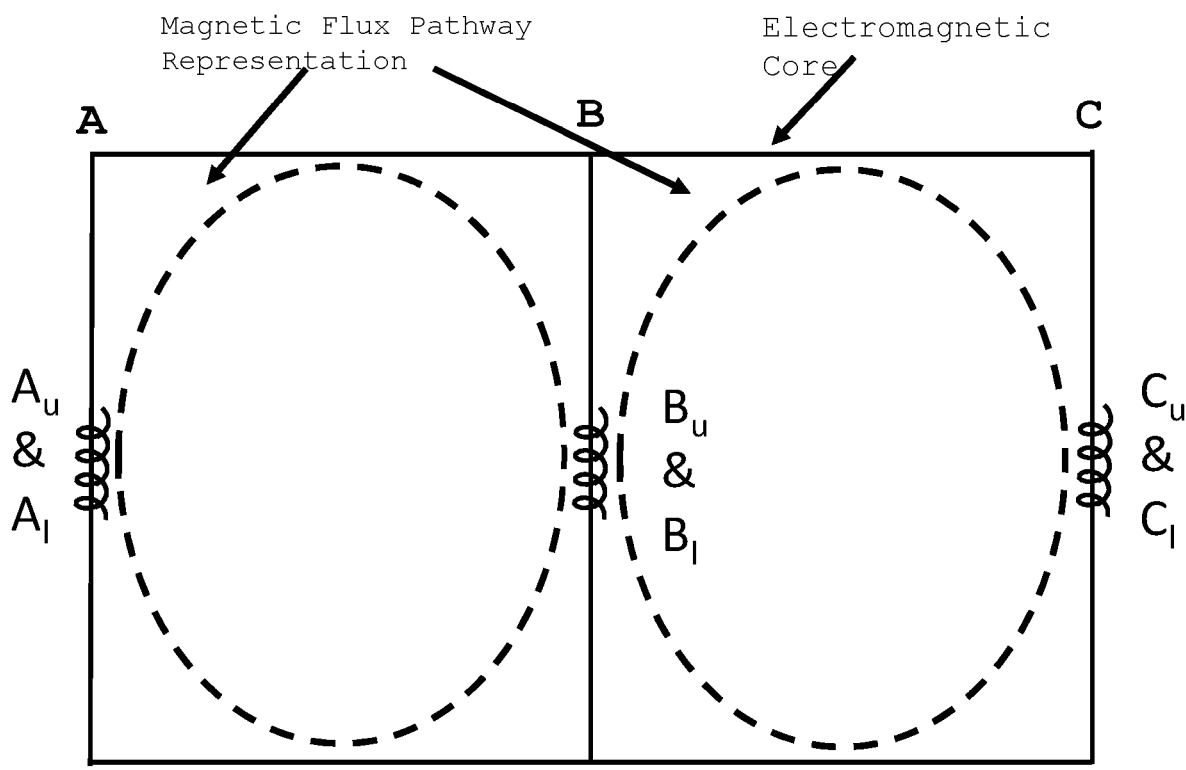
FIG. 14 is a two-dimensional single line representation of a standard three phase transformer with concentric primary and secondary windings.

When the single line diagram of FIG. 2 is drawn as a two-dimensional representation it is displayed as shown in FIG. 3. It will be appreciated that the single line diagram of FIG. 2 (and the single line diagrams of at least FIGS. 3, 9 and 14 are representations of the arrangements of the coils of the device (i.e. a magnetic circuit diagram), and are as such, different to an electronic circuit diagram.

It will be apparent to those skilled in the art that different physical geometries can be used to provide the electromagnetic Delta core 100 for the device. Another such geometry is shown in FIG. 9. Any such geometry which provides the equivalent magnetic connections and coil arrangements can be used without deviating from the scope of this invention.

Figure 10:
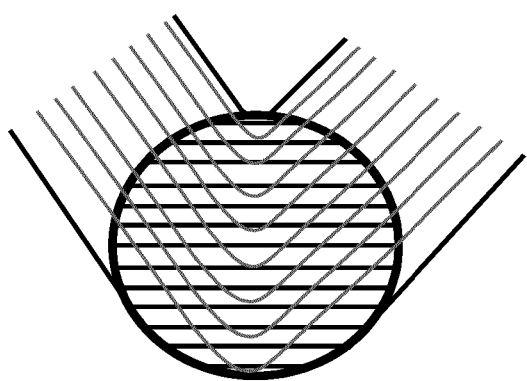
FIG. 10 is a circular cross section at the top of one of the limbs of the three phase core made of stacked laminates, with the upper shell made of stacked laminates on top providing the magnetic connection between the limb and the upper shell.

The construction of the electromagnetic core 100 is completed with stacked laminates of a magnetic steel to create a circular cross section for the limbs 10A, 10B, 10C. Alternatively, any shape cross section can be used for limbs 10A, 10B, 10C. The upper and lower shells 12, 14 are created using wound laminates of electromagnetic steel. The limbs 10A, 10B, 10C and upper and lower shells 12, 14 can be clamped together to provide a magnetic connection between them. FIG. 10 shows a top down view of the upper ring laminates on top of one of the limbs.

Figure 11:
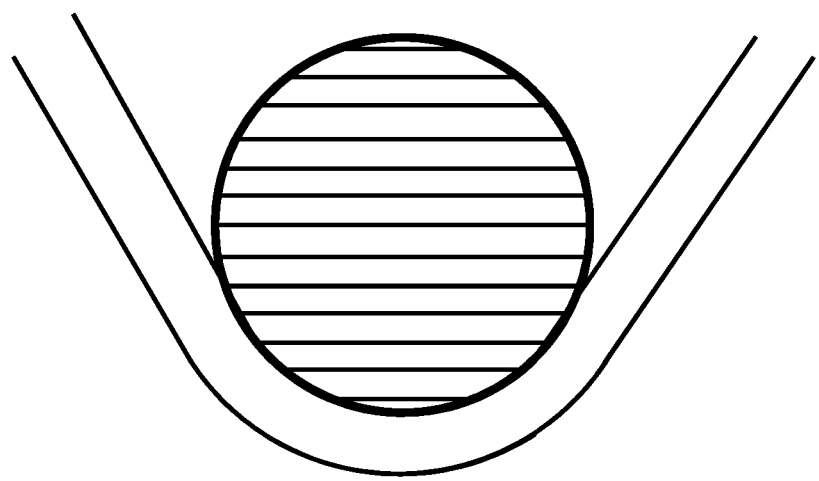
FIG. 11 is a circular cross section at in the middle of one of the limbs of the three phase core made of stacked laminates, with the transfer ring wrapped around the limb providing the magnetic connection between the limb and the transfer ring.

The transfer ring is also constructed of wound laminates of electromagnetic steel, wrapped around the outside of the three limbs. FIG. 11 shown a single limb with the transfer ring wrapping around the outside forming an angle of 120 degrees. The laminates of the transfer ring are not shown.

Figure 12:
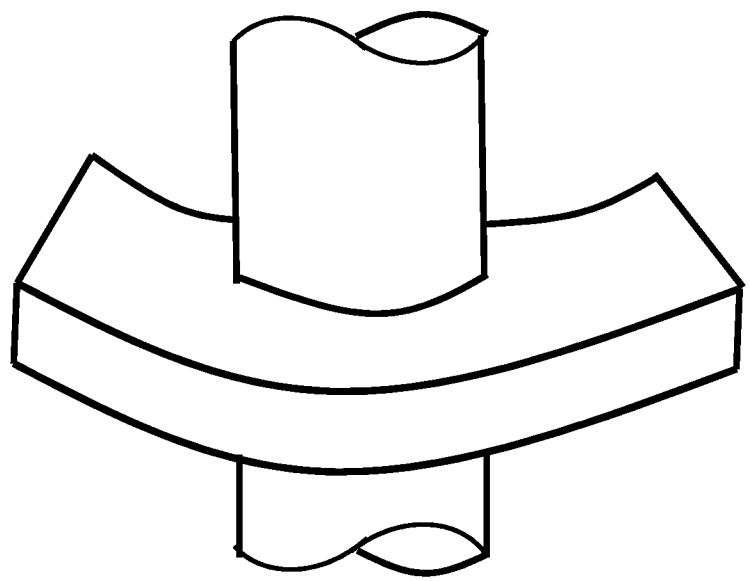
FIG. 12 is a three dimensional diagram of one of the limbs split into a lower and upper portion, divided by the transfer ring, providing the magnetic connection between the limb and the transfer ring.

Alternatively each of the limbs 10A, 10B, 10C can be divided into two individual limbs, one with the upper coils and one with the lower coils as shown in FIG. 12. These are separated by the transfer ring 16 which is constructed using wound laminates of electromagnetic steel in the same manner as the upper and lower shell. This is all clamped together within the same clamping arrangement as used for the upper and lower shells.

Figure 19:
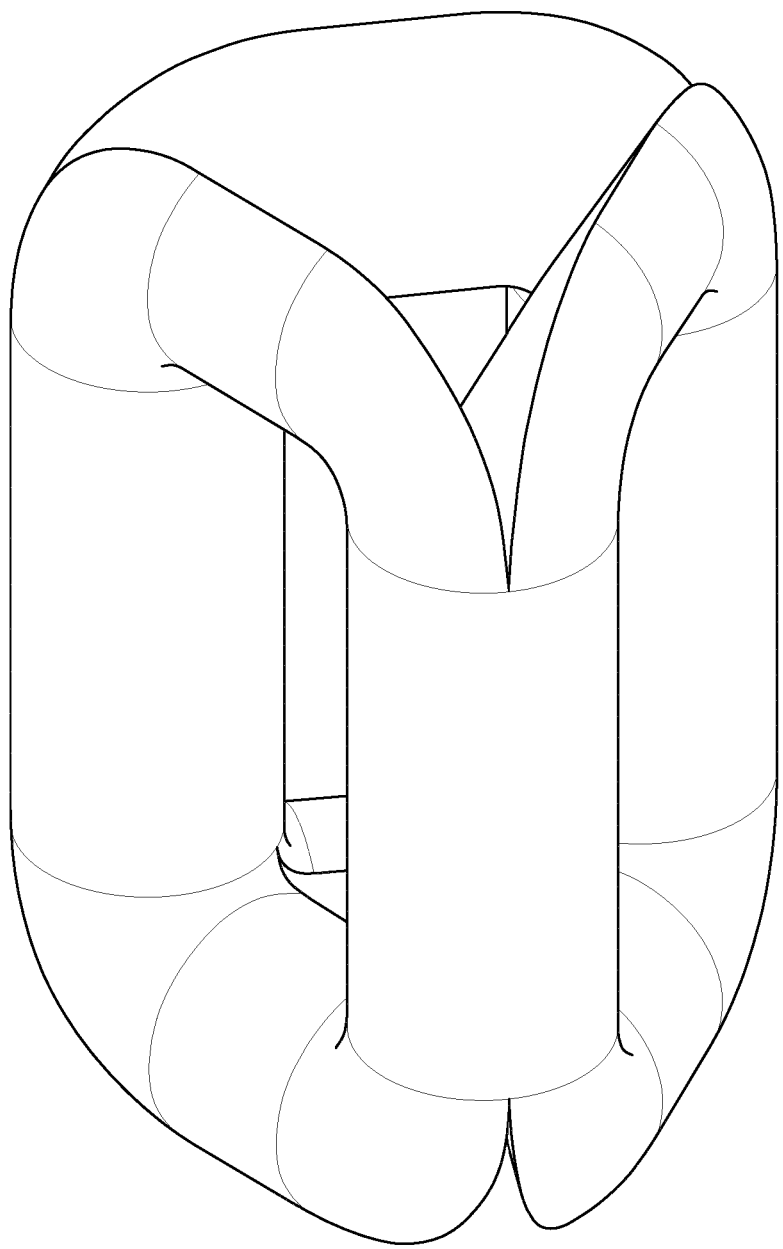
FIG. 19 is a three-dimensional diagram of a core manufacturing geometry in accordance with some embodiments of the present invention.

Alternatively, the Delta core can be manufactured by connecting three core type single phase transformers together in an arrangement shown in FIG. 19. The transfer ring 16 can be added to this core by winding the laminate around the outside of the core as shown in FIG. 11.

Figure 20:
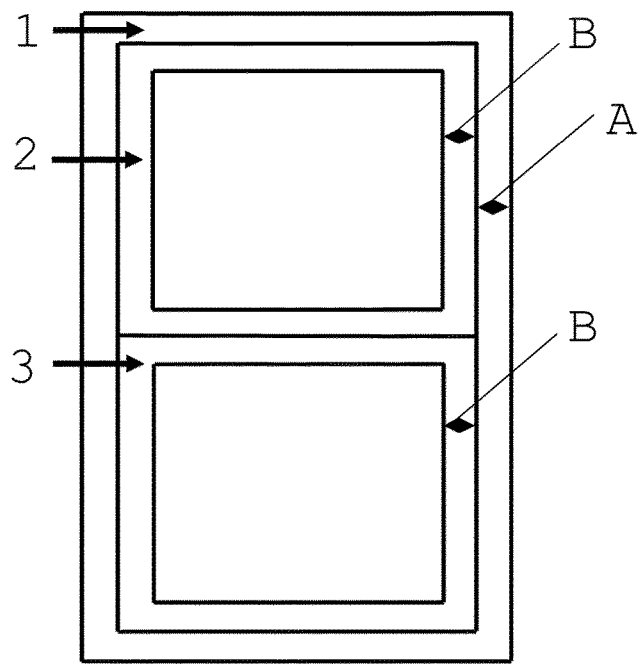
FIG. 20 is a cross section diagram of a single phase of the electromagnetic core consisting of three individual parts combined together in accordance with some embodiments of the present invention.

Alternatively, the Delta core can be manufactured using the arrangement shown in FIG. 19, with each single-phase core type transformer being manufactured as shown in FIG. 20. This consists of 3 individual cores (labelled 1, 2, and 3) wound and connected to form the single-phase core and arm of the transfer ring. Cores 2 and 3 have cross-sectional area of B, and core 1 has a cross-sectional area of A. When connected in the arrangement shown in FIG. 20 the single-phase core has a consistent outer cross-sectional area of A+B, and a transfer ring cross-sectional area of 2B. When three single-phase cores are connected together as shown in FIG. 19, each of the limbs 10A, 10B, 10C has a cross-sectional area of 2A+2B.

It will be apparent to those skilled in the art that a number of different manufacturing and assembly techniques can be used to create an electromagnetic core 100 of this general description.

Electromagnetic Core Star Arrangement

Figure 27:
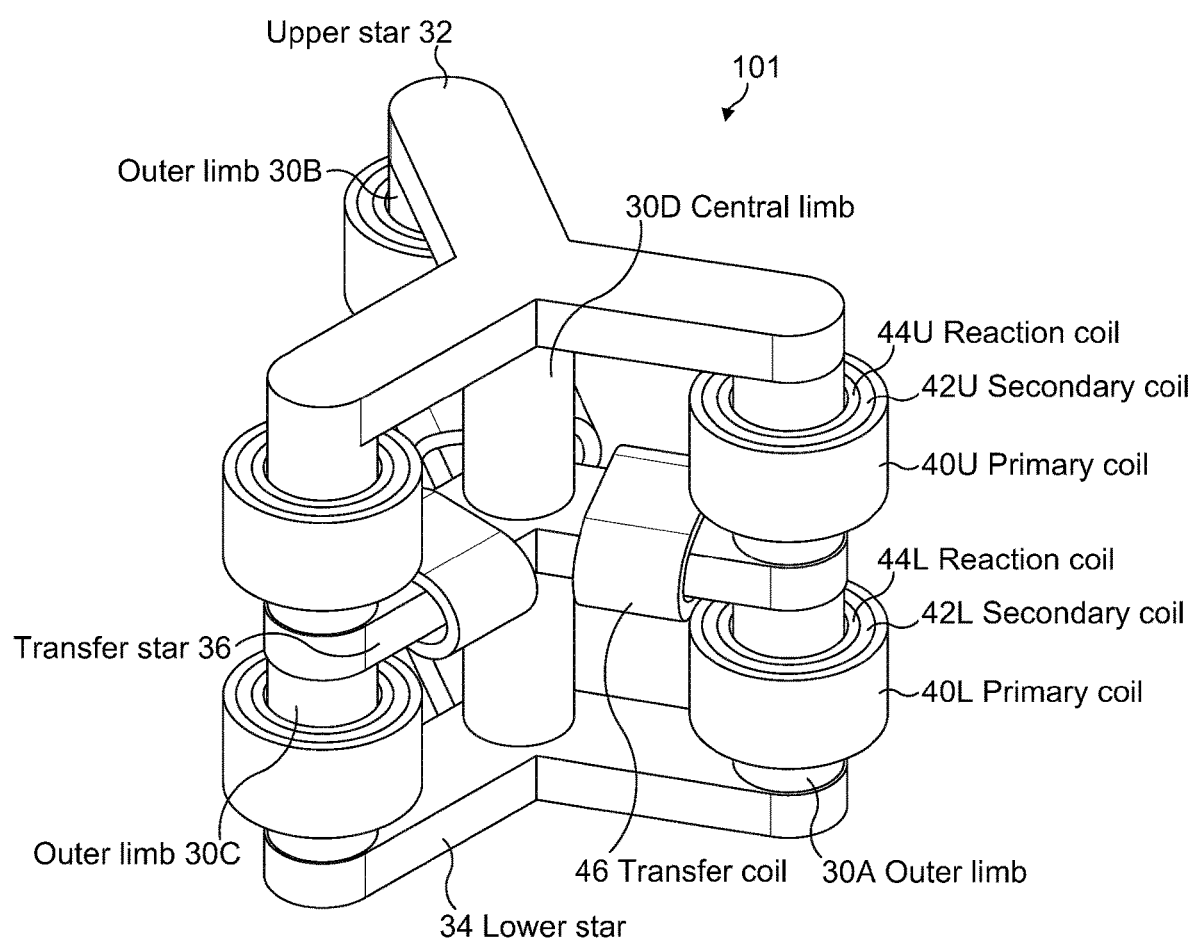
FIG. 27 is a three-dimensional diagram of the electromagnetic core and windings in accordance with some embodiments of the present invention.

Another electromagnetic core (transformer apparatus) 101 of the device is shown in FIG. 27. It includes a central limb 30D, and three outer limbs 30A, 30B, 30C, one for each phase of the three-phase power flowing through the device (Phase A, B, and C). These four limbs are connected at one end by a top three point star 32, and at the other end by a bottom three point star 34. This provides a magnetically symmetrical core for all three phases A, B, C. The electromagnetic core 101 shown in FIG. 27 is provided in a star formation, hereby called an electromagnetic star core, or Star core. A transfer star 36 is connected to each of the four limbs 30A, 30B, 30C, 30D between the upper and lower stars 32, 34, providing an additional pathway for magnetic flux to flow. The core 101 may be made of any magnetic material whose including but not limited to ferromagnetic materials. The core itself may be formed as a unitary structure, or may be constructed from multiple component parts, which may be made from the same or different materials for different regions of the magnetic core.

In the embodiment of FIG. 27, the central limb 30D is located at a geometric centre defined by the three outer limbs 30A, 30B, 30C. In the embodiment of FIG. 27, each outer limb 30A, 30B, 30C is arranged about the central limb 30D at an equal distance from the central limb 30D (i.e. a constant radius). The outer limbs 30A, 30B, 30C, are spaced apart about the central limb 30D by 120°. Of course, in other embodiments, the outer limbs 30A, 30B, 30C may be spaced apart about the central limb 30D by different angles and/or distances such that the limb 30D is not located at the geometric centre (i.e. an inner limb rather than a central limb).

Each outer limb 30A, 30B, 30C has two sets of concentrically wound coils, one above the transfer star 36 and one below. The upper coil on the phase A limb is denoted $A_u$, the lower coil on the phase A limb is denoted $A_l$. Likewise phase B and C coils are denoted $B_u$, $B_l$, $C_u$, and $C_l$. Each set of concentrically wound coils has three separate coils, a primary 40U, 40L, a secondary 42U, 42L, and a reaction coil 44U, 44L. Each pair of primary coils on a limb are connected in series. Each pair of secondary coils on a limb are connected in series. Each pair of reaction coils may be connected in series, or each reaction coil may be independently connected to control circuitry. The transfer star has three transfer coils 46 wound on it, one on each of the arms of the star. These are denoted $T_A$, $T_B$, and $T_C$. A three-dimensional single line diagram of the Star electromagnetic core with these coil labels is shown in FIG. 28.

In total there are 21 coils on the electromagnetic star core. These coils can be wound in different manners as would a standard transformer coils be wound. These include helical, disc, cylindrical, and crossover, as described at https://www.electrical4u.com/transformer-winding/ for example.

Figure 28:
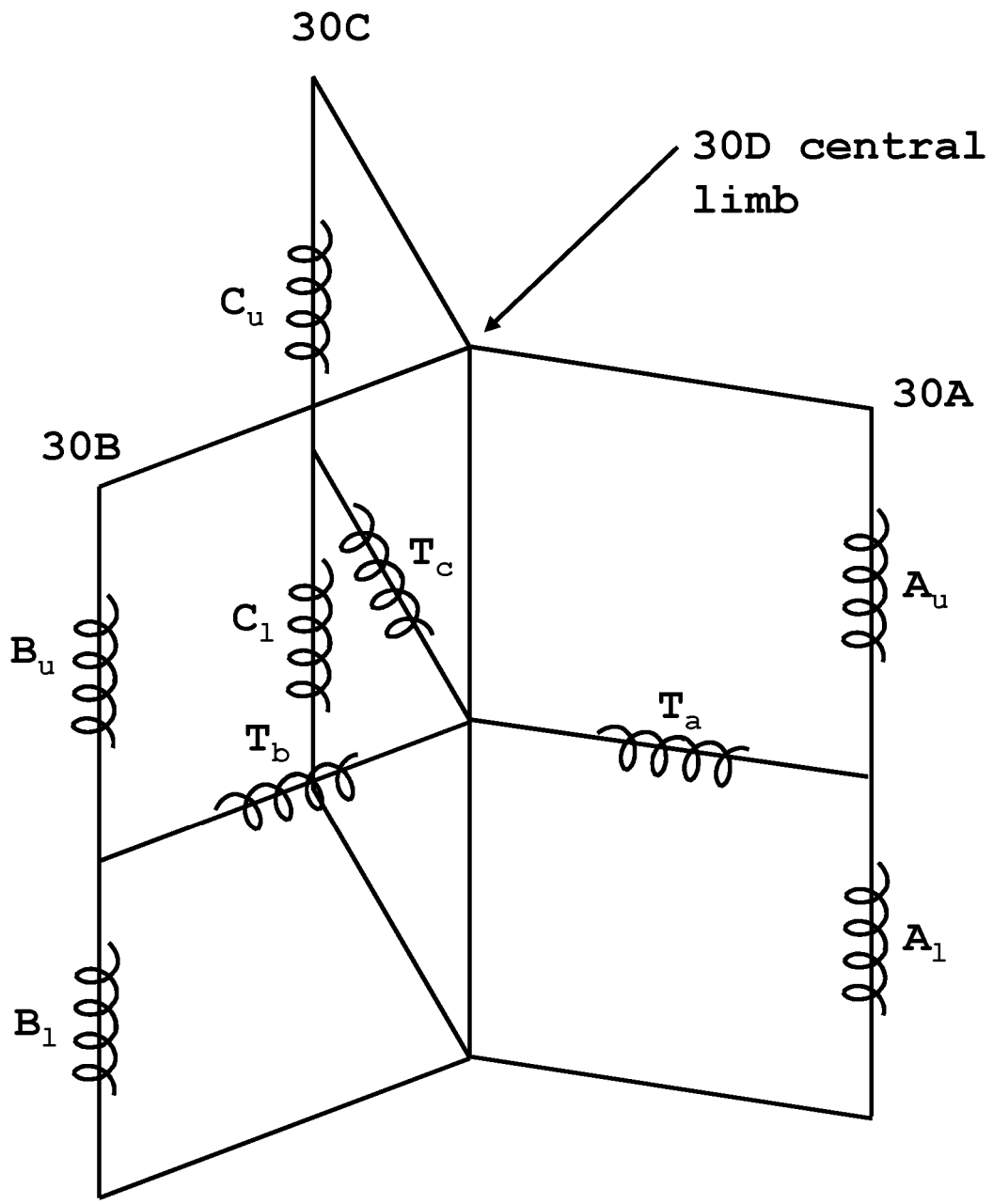
FIG. 28 is a three-dimensional single line diagram of the electromagnetic core windings in accordance with some embodiments of the present invention.
Figure 34:
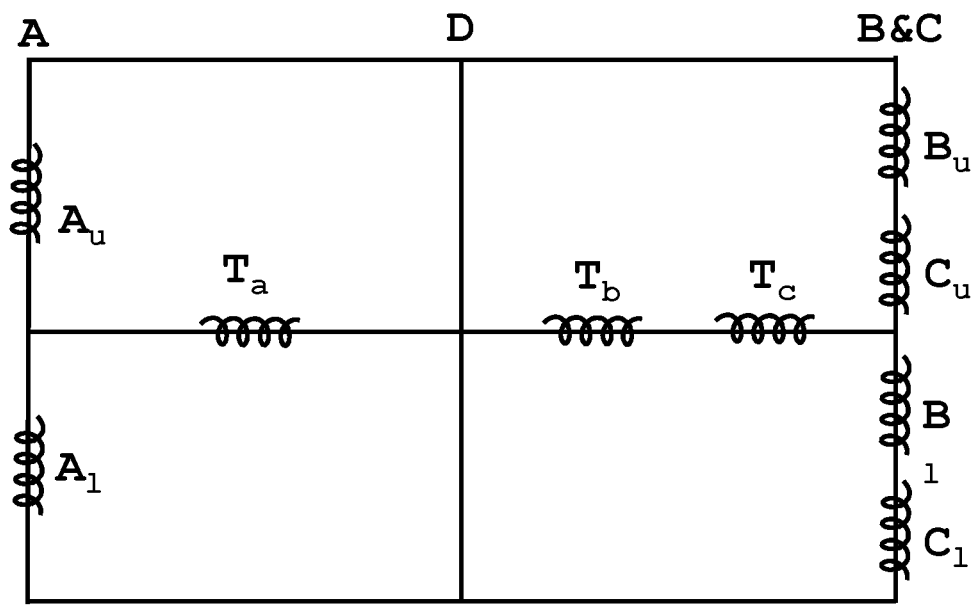
FIG. 34 is a two-dimensional single line representation of the electromagnetic core windings from the perspective of phase A in accordance with some embodiments of the present invention.
Figure 35:
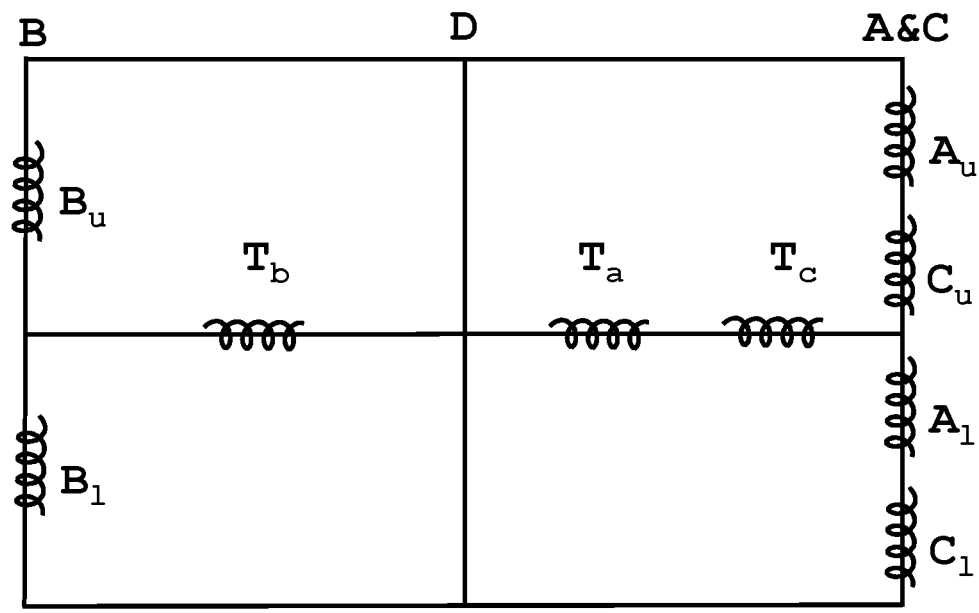
FIG. 35 is a two-dimensional single line representation of the electromagnetic core windings from the perspective of phase B in accordance with some embodiments of the present invention.
Figure 36:
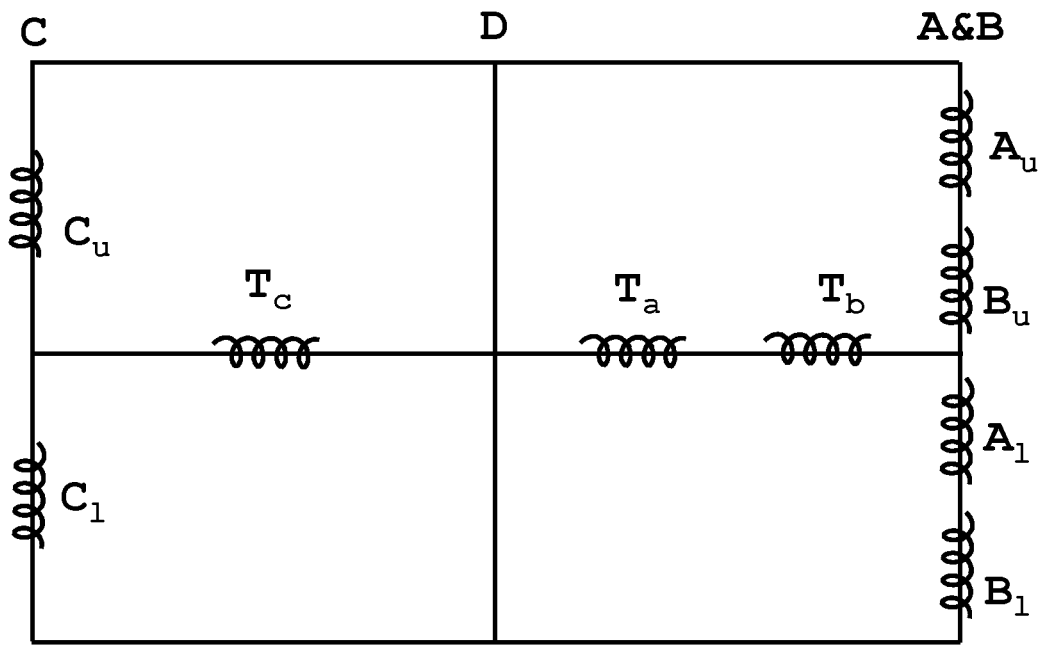
FIG. 36 is a two-dimensional single line representation of the electromagnetic core windings from the perspective of phase C in accordance with some embodiments of the present invention.

When the single line diagram of FIG. 28 is drawn as a simplified two-dimensional representation it can be displayed as shown in FIG. 34, FIG. 35, and FIG. 36. Each of FIGS. 34, 35, and 36 show one of the three phases of the device on one of the outer limbs. Each phase is connected to the same central limb 30D. Within a traditional 3 phase transformer the energy from each phase flows equally between the remaining two phases outer limbs before completing the circuit back to it's original outer limb. This results in half of the energy passing through each of the remaining two outer limbs. As an example for a traditional 3 phase transformer, in FIG. 34, all energy flows through $A_u$ and $A_l$, half the energy flows through $B_u$ and $B_l$, and half the energy flows through $C_u$ and $C_l$. For the Star core, the addition of the central limb 10D may change the behaviour of the flux so that the flux for each phase passes only through the outer limb for that phase and the central limb 30D. As such, each of the 3 phases can be controlled independently using the transfer coils 46.

It will be appreciated that the single line diagram of FIG. 28 (and the single line diagrams of FIGS. 34, 35, 36, and 32) are representations of the arrangements of the coils of the device (i.e. a magnetic circuit diagram), and are as such, different to an electronic circuit diagram.

The diagrams FIG. 27 and FIG. 28, show a star core arrangement with the 3 phases spaced equidistant at 120 degrees from each other. It will be apparent to those skilled in the art that in other embodiments any set of angles can used to separate the limbs of the device without deviating from the scope of this device.

In the embodiment of FIG. 27, the three limbs 30A, 30B, 30C are arranged at 120 degree intervals about the central limb. In some embodiments, the three limbs are arranged at arranged at 120 degree intervals about the central limb at equal distances. Accordingly, the primary coils, secondary coils and reaction coils for each limb are spaced apart at 120° intervals. This core and windings arrangement provides a symmetric relationship between all three phases. The magnetic flux of all three phases passes through the central limb of the core at all times. When balanced, three phases power consists of the three phases each being 120 degrees out of phases with each other. This results in the central limb of the core having a net flux of zero passing through it. If the phases are out of balance, the net flux flowing through the central limb may be representative of the out of balance component. This is a result of the unique geometry arrangement of the core.

Three the limbs 30A, 30B, 30C may be connected to the central limb 30D with any angles and distance without deviating from the scope of this invention.

The construction of the Star electromagnetic core 101 is completed with stacked laminates of a magnetic steel to create a circular cross section for the limbs 30A, 30B, 30C, 30D. Alternatively, any shape cross section can be used for limbs 30A, 30B, 30C, 30D.

The upper and lower stars 32, 34 are created using stacked laminates of electromagnetic steel. The limbs 30A, 30B, 30C, 30D and upper and lower shells 32, 34 can be clamped together to provide a magnetic connection between them.

The transfer star is constructed of wound laminates of electromagnetic steel. Each arm of the star is wrapped around the central limb 30D and the corresponding outer limb 30A, 30B, 30C. Each arm of the transfer star can be wrapped at any height on the central limb 30D provided it is between the upper and lower coils on that limb. For example, the arm connecting 30D and 30A must be at a height to physically connect between coils $A_u$ and $A_l$.

Figure 31:
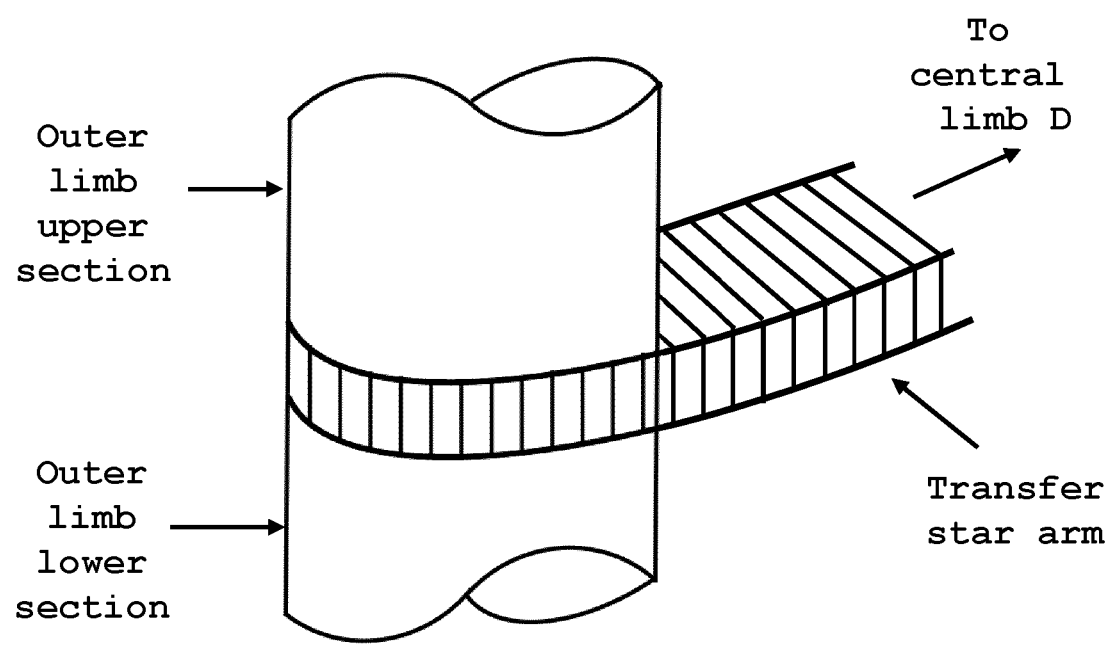
FIG. 31 is a three dimensional diagram of one of the outer limbs split into a lower and upper portion, divided by the transfer star, providing the magnetic connection between the limb and the transfer star.

Alternatively, each of the limbs 30A, 30B, 30C, 30D can be divided into two individual limbs, one with the upper coils and one with the lower coils as shown in FIG. 31. These are separated by the transfer star 36 which is constructed using stacked laminates of electromagnetic steel in the same manner as the upper and lower star. This is all clamped together within the same clamping arrangement as used for the upper and lower stars.

Alternatively, the Star core can be manufactured by connecting three single-phase core transformers shown in FIG. 20. Each of these single-phase transformer cores consists of 3 individual cores (labelled 1, 2, and 3) wound and connected to form the single-phase core and arm of the transfer star. Cores 2 and 3 have cross-sectional area of B, and core 1 has a cross-sectional area of A. When connected in the arrangement shown in FIG. 20 the single-phase core has a consistent outer cross-sectional area of A+B, and a transfer star cross-sectional area of 2B. When three single-phase cores are connected together to form a star core, each of the limbs 30A, 30B, 30C has a cross-sectional area of A+B, and the central limb 30D has a cross sectional area of 3A+3B.

It will be apparent to those skilled in the art that a number of different manufacturing and assembly techniques can be used to create an electromagnetic star core 101 of this general description.

Power Electronics

Power electronics 104 are used to provide the power flowing through the transfer coils 26 of electromagnetic core 100 or the transfer coils 46 of the electromagnetic core 101, where energising the transfer coils 26, 46 with the appropriate timing will allow flux to be injected or extracted from each phase, or when short-circuited will prevent flux flowing between phases through the transfer ring 16 or transfer star 36 and result in the device operating as a fixed ratio power transformation device like a standard transformer. This provides a failsafe mode for the device, should the power electronics have a fault the transfer coils 26 on the electromagnetic delta core 100, or the transfer coils 46 on the electromagnetic star core 101 will be short-circuited and the device will operate as a standard transformer.

The power electronics 104 use the switching of electronic transistors to modulate the power flow output. These gates can be different types depending on the power rating and switching speed required for a particular size and performance of the power flow transformation device. It will be apparent to those skilled in the art that transistors such as IGBT (insulated-gate bipolar transistor) or mosfet (metal-oxide-semiconductor field-effect transistor) can be used for this application. Other technologies such as Silicon Carbide and Gallium Nitride are also in development in the field and can be used.

Figure 13:
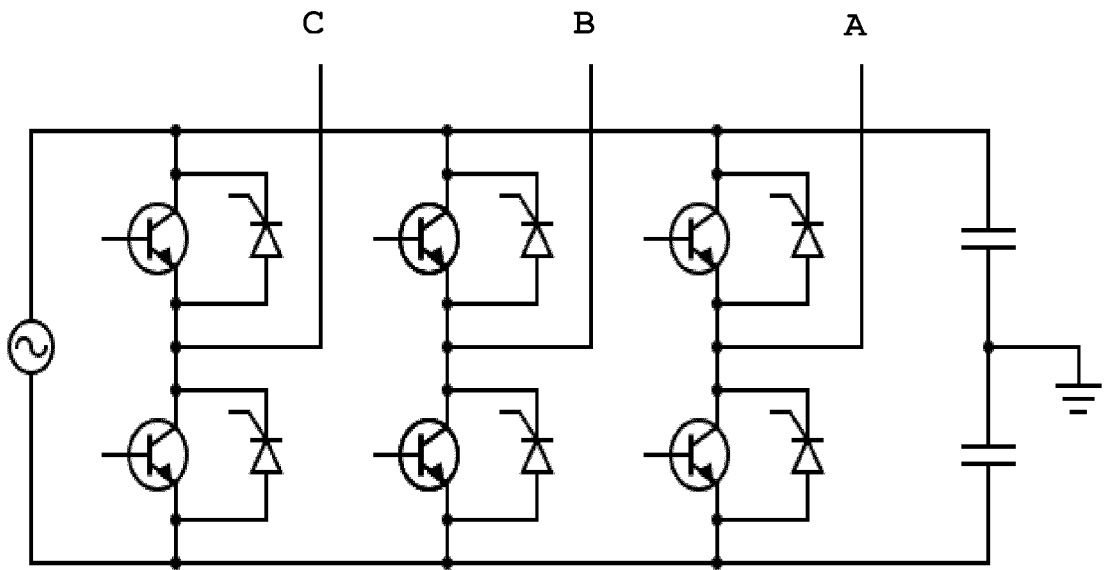
FIG. 13 is a circuit diagram of the power electronics approach to provide the pulse width modulation of the three transfer coils.
Figure 17:
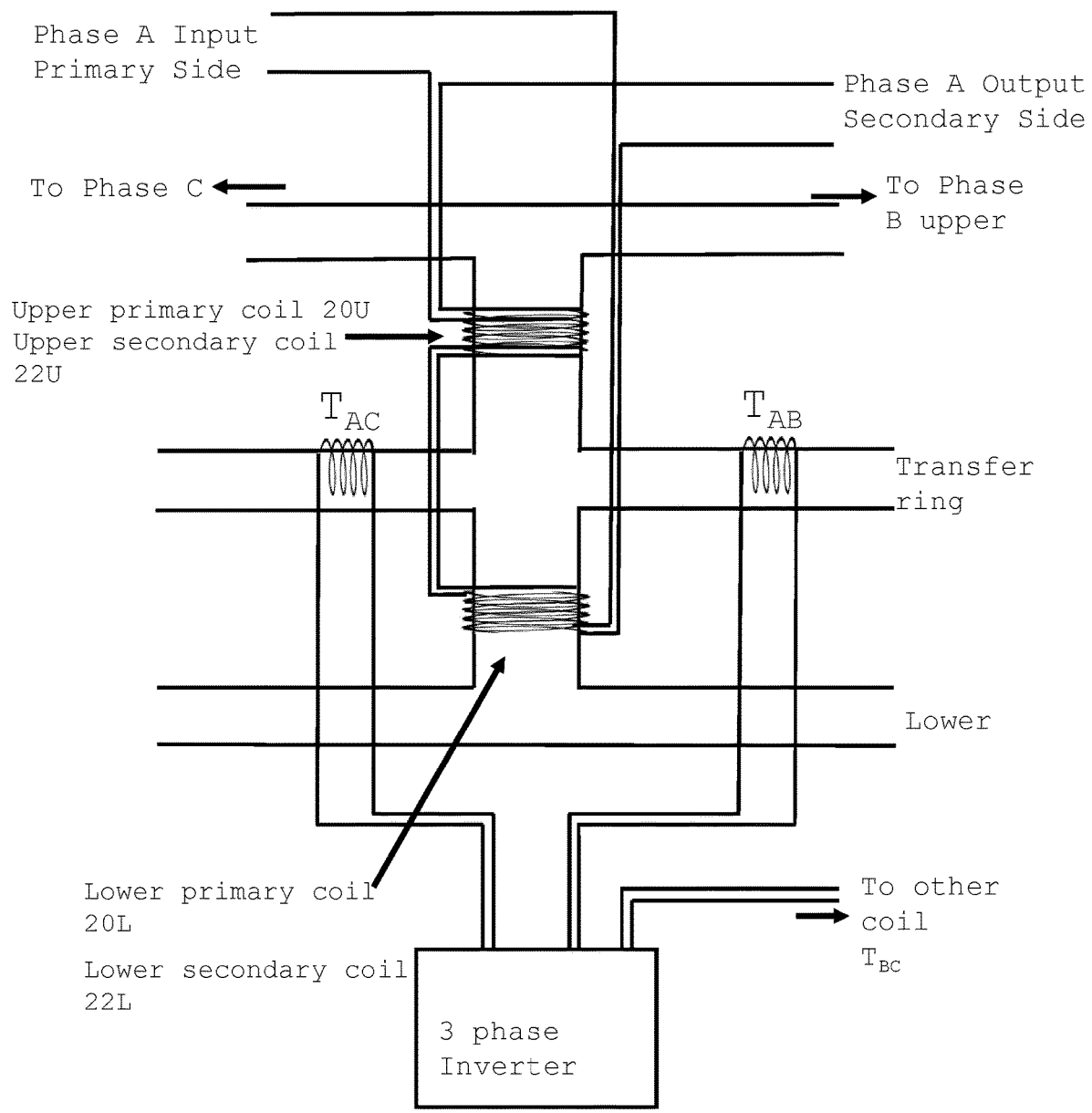
FIG. 17 is a diagram of a single phase of the electromagnetic core, with the primary and secondary coils connected to the electricity grid, and control coils connected to the power electronics.
Figure 18:
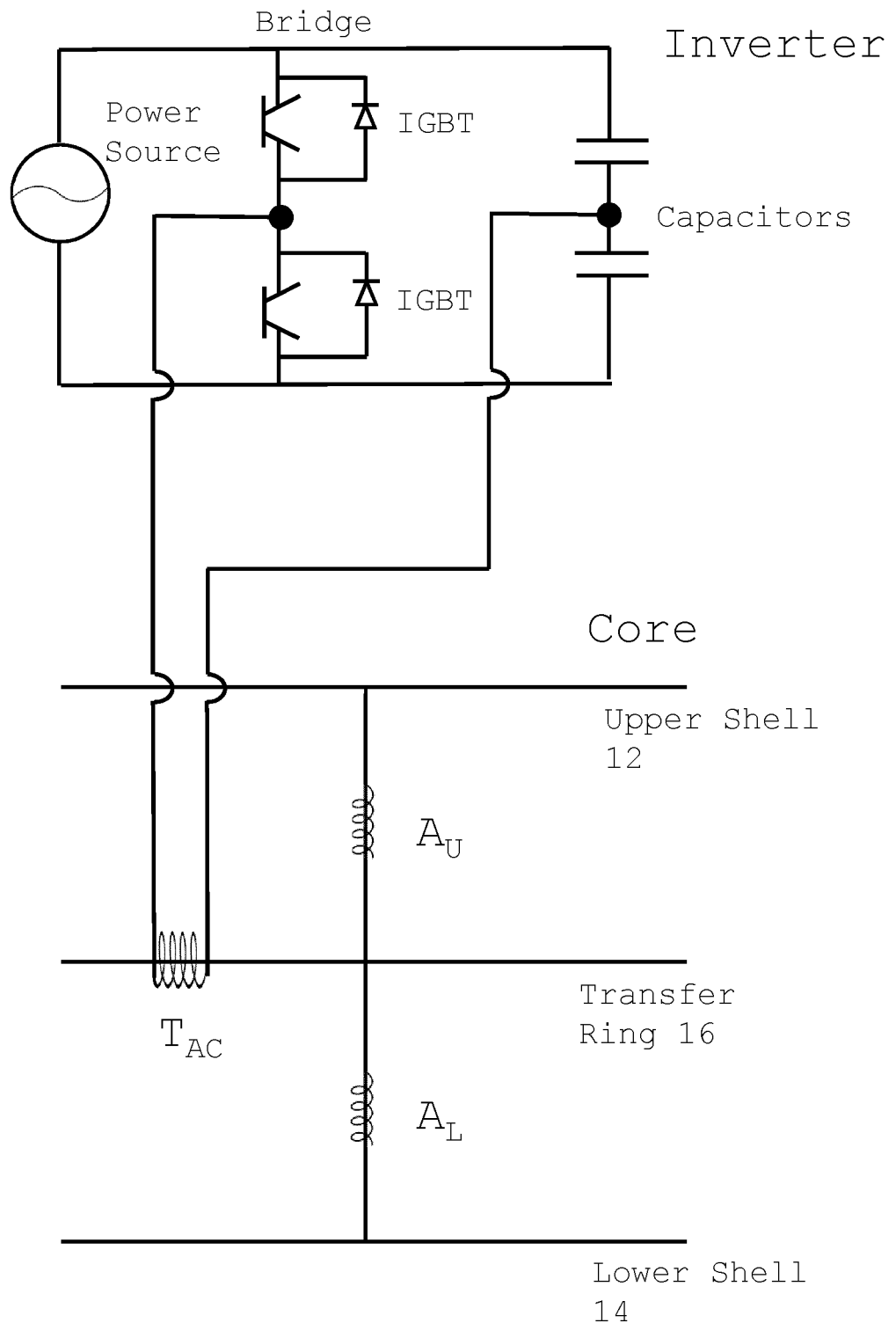
FIG. 18 is a circuit diagram of a single phase of the device, showing the transfer coil on one side of the transfer ring connected to one of the bridges in the power electronics.

For the Delta core, the transistors for the power electronics 104 are arranged as shown in FIG. 13 and switched on and off by the controller in order to provide the desired power level in the transfer coil. The outputs in FIG. 13 are connected to the transfer windings shown in FIG. 3, where output A is connected to coil $T_{AC}$, output B is connected to coil $T_{AB}$, and output C is connected to coil $T_{BC}$. A single phase of this is shown in FIG. 17 and FIG. 18.

Figure 32:
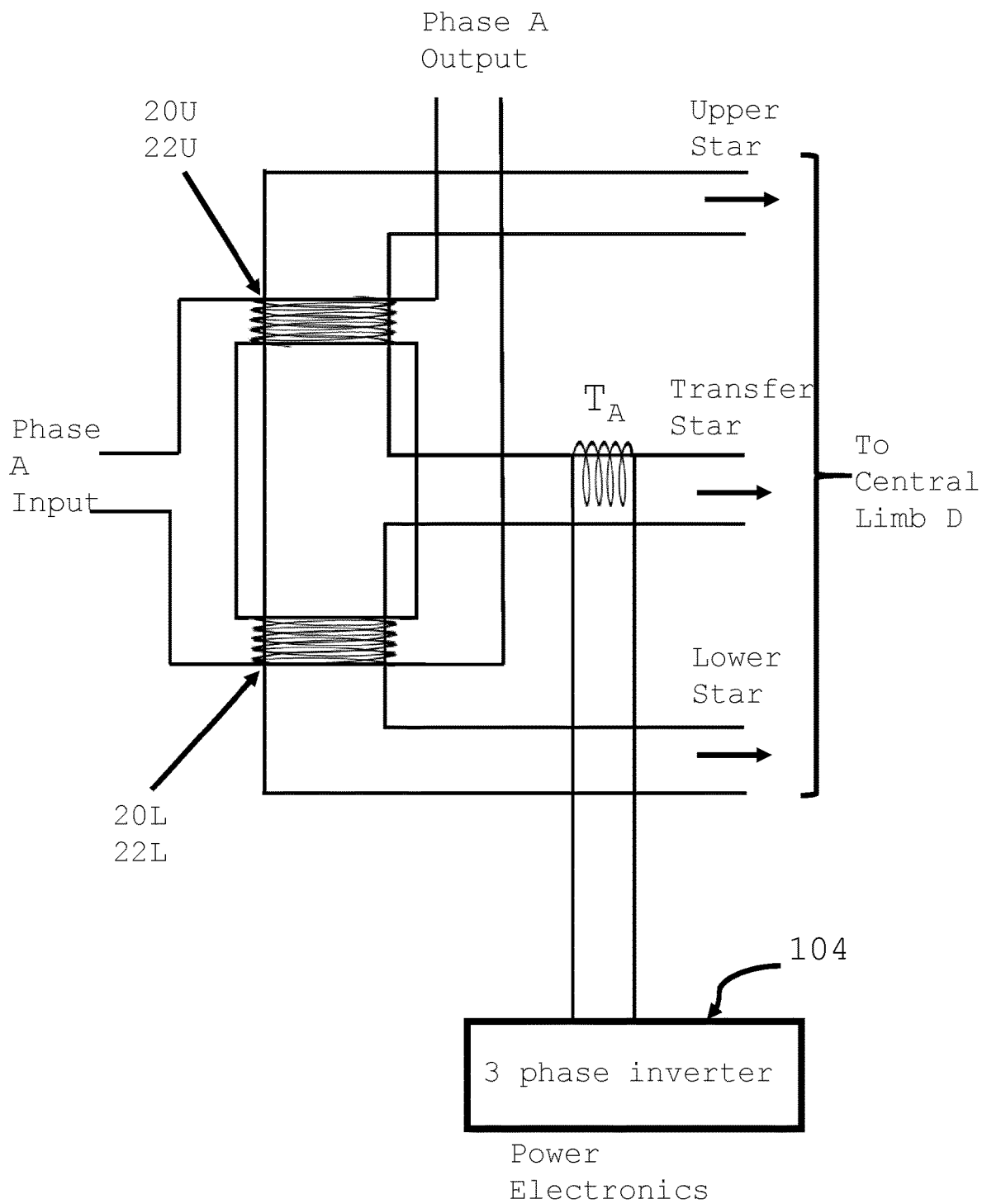
FIG. 32 is a diagram of a single phase of the electromagnetic core, with the primary and secondary coils connected to the electricity grid, and transfer coil connected to the power electronics.
Figure 33:
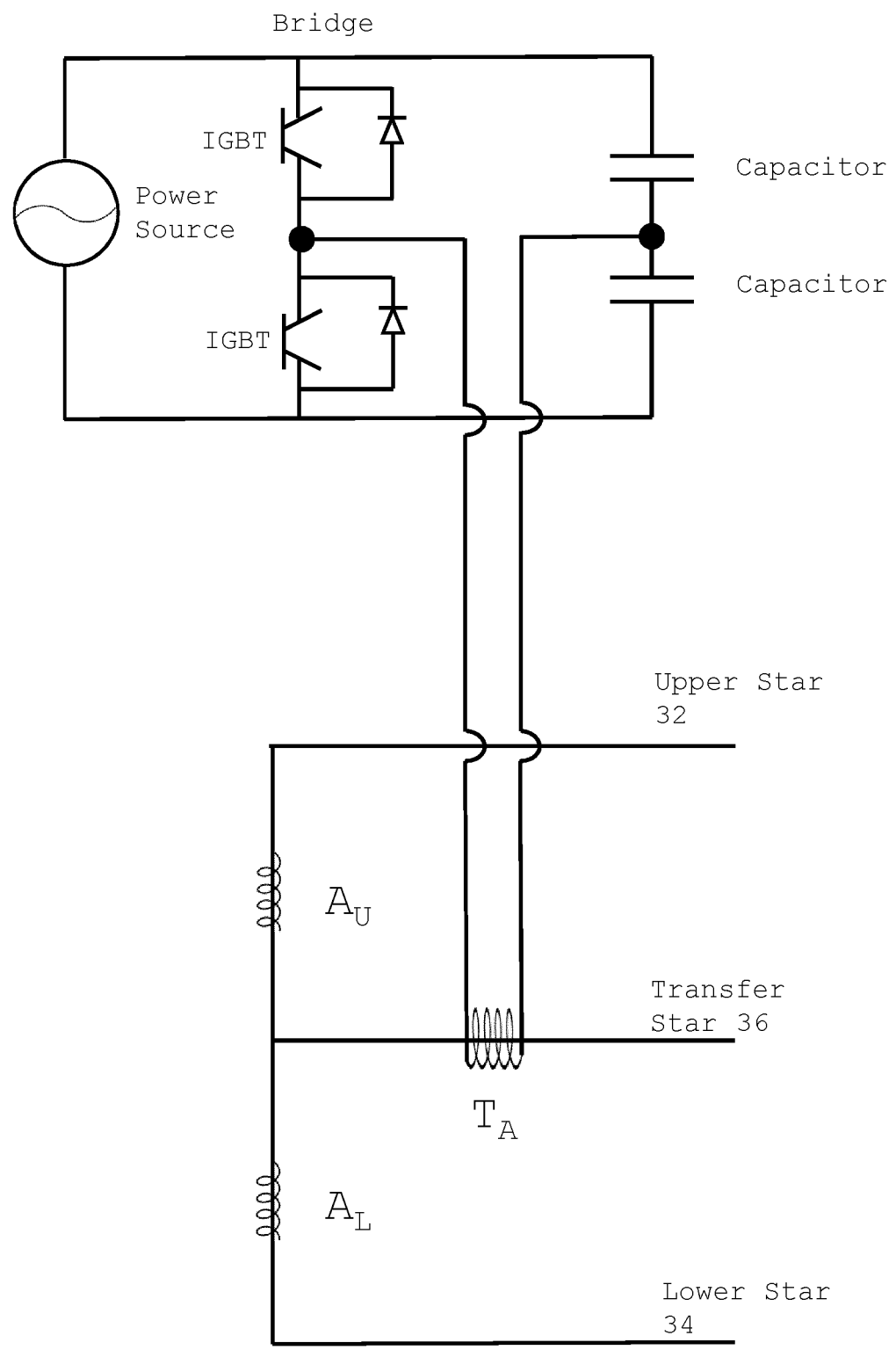
FIG. 33 is a circuit diagram of a single phase of the device, showing the transfer coil on the transfer star connected to one of the bridges in the power electronics.

For the Star core, the transistors for the power electronics 104 are arranged as shown in FIG. 13 and switched on and off by the controller in order to provide the desired power level in each arm of the transfer star 36. The outputs in FIG. 13 are connected to the transfer windings shown in FIG. 28, where output A is connected to coil $T_A$, output B is connected to coil $T_B$, and output C is connected to coil $T_C$. A single phase of this is shown in FIG. 32 and FIG. 33.

The power electronics 104 include two bridges, capacitors, and a common neutral for all three phases. In some embodiments, the power electronics 104 may include two half bridges for each phase, capacitors and a common neutral. It will be obvious to those skilled in the art that many different transistor arrangements can be used, such as full bridges, to achieve the same effect and desired functionality for the device without deviating from the scope of this invention.

It is also possible to add energy storage into the power electronics circuit. This can be in the form of capacitors, or chemical energy storage such as Lithium-Ion batteries. The energy storage device would be able to be charged by the power electronics using power flowing through the device and create an energy reserve. This reserve could be drawn upon if required in order to meet the target output when there is not enough input power from the primary coil. The level and duration of this capability is directly proportional to the quantity of energy stored. For example, in some embodiments, such as in FIG. 13 capacitors forming a DC link are shown.

As an example, the energy storage could be trickle charged on device power up. If the output power is higher than the input power received, additional energy can be injected into the device by the controller using the energy storage. This allows the output of the device to maintain the desired level without impacting the upstream energy system. This could occur whilst there is stored energy remaining in the device. If there is no energy in the storage, the device will operate as it would without energy storage. When there is excess available power on the input, the controller will charge the energy storage for later use.

The energy storage will be charged by the power electronics circuit, and injected into the device when needed through the transfer coils.

The transistors are controlled using a high speed microprocessor (the controller 102) such as the 100 MHz Texas Instruments device described at http://www.ti.com/product/TMS320F2808, powered from the power flow through the device, and the electrical power supply processes are implemented as configuration data stored in non-volatile memory. The microprocessor executes a control process to PWM the transistors in the bridge circuits shown in FIG. 13. The control algorithm operates at a speed of 50 kHz, or three orders of magnitude higher than the fundamental frequency of the power waveform it is controlling (50 Hz). The control algorithm can operate at a higher or lower frequency. A lower frequency can be used depending on the resolution and accuracy of the control required. A higher frequency can be used and will be limited by the capabilities of the control hardware utilised. A faster control algorithm will result in more immediate and accurate control. It will be obvious to those skilled in the art that other technologies can be used in place of a microprocessor, such as a field programmable gate array (or FPGA) without deviating from the scope of the invention. It will also be apparent to those skilled in the art that in other embodiments the controller may be powered by a separate local power supply where available, such as local control power from a distribution board.

Voltage Control

Electric power flows through the primary coils 20U, 20L or 40U, 40L which generates a magnetic flux that flows through the magnetic core and generates an electric current in the secondary coils 22U, 22L or 42U, 42L. For a standard three-phase transformer with concentric primary and secondary coils on each phase, the flux flows through the pathways shown in FIG. 14.

For each phase of the device, the primary and secondary coils for the power flow transformation device are split for each phase, one coil above the transfer ring (the upper coil) and one coil below the transfer ring (the lower coil), as shown in FIG. 1 for the Delta core and FIG. 27 for the Star core. The upper and lower coil are electrically connected in series. The number of turns in the upper and lower coil for the primary and secondary are different:

Primary upper coil turns: $P_u = N_1 \cdot n$

Secondary upper coil turns: $S_u = N_2 \cdot (1-n)$

Primary lower coil turns: $P_l = N_1 \cdot (1-n)$

Secondary lower coil turns: $S_l = N_2 \cdot n$

Where $0 < n < 1$

N1 is the total number of turns the primary coil has for that phase, and N2 is the total number of turns the secondary coil has for that phase.

As the power electronics 104 controls the power in the transfer coils on the transfer ring 16 or transfer star 36, a mmf is generated through the transfer ring or transfer star.

Magnetomotive force (mmf)=NI ampere-turns (At), where N=number of conductors (or turns) and I=current in amperes.

Due to Lenz's law additional mmf to be added into the magnetic circuit for that phase between the upper and lower coil, and will be flow evenly between the two pathways to the upper and lower coils.

The voltage at the upper coil will be $-N1 \cdot \dfrac{d\phi_u}{dt}$

The voltage at the lower coil will be $-N2 \cdot \dfrac{d\phi_l}{dt}$

Where $\phi_u$ is the flux through the upper coil, and $\phi_l$ is the flux through the lower coil. The flux generated from the primary to secondary connection $\phi_0$ is the same for both the upper and lower coils. The flux generated from the transfer coils are equal but in opposite directions. Therefore:

$\phi_u = \phi_0 - \partial\phi$ $\phi_l = \phi_0 + \partial\phi$

As an example, the power flow transformation device can have a value of n=⅔, $N_1$=60, $N_2$=30. Then:

$P_u = N_1 \cdot n = 60 \cdot \tfrac{2}{3} = 40$ turns $S_u = N_2 \cdot (1-n) = 30 \cdot (1-\tfrac{2}{3}) = 10$ turns $P_l = N_1 \cdot (1-n) = 60 \cdot (1-\tfrac{2}{3}) = 20$ turns $S_l = N_2 \cdot n = 30 \cdot \tfrac{2}{3} = 20$ turns When the transfer coils are short-circuited and there is no additional mmf in the phase, the voltage transformation will be $N_1:N_2$, or 60:30=2:1 (i.e. 200V on primary will produce 100V on the secondary).

When additional mmf is provided to the magnetic circuit through the transfer ring it will impact the flux flowing through the upper and lower coils in equal but opposite ways as described earlier. If this mmf produces the equivalent of a 10% change in each, then:

$P_u = N_1 \cdot n = 60 \cdot \tfrac{2}{3} - 10\% = 36$ turns $S_u = N_2 \cdot (1-n) = 30 \cdot (1-\tfrac{2}{3}) - 10\% = 9$ turns $P_l = N_1 \cdot (1-n) = 60 \cdot (1-\tfrac{2}{3}) + 10\% = 22$ turns $S_l = N_2 \cdot n = 30 \cdot \tfrac{2}{3} + 10\% = 22$ turns Therefore the voltage transformation will be $N_1:N_2$, or 36+22:9+22=58:31 (i.e. 200V on primary will produce 106.9V on the secondary).

If n=0.5 then both the upper and lower coils have the same number of turns, and the voltage control methodology will not work.

Because the additional mmf that produces this voltage transformation change comes from the other phases and returns to the other phases through the magnetic core, the entire process conserves energy and is extremely efficient.

For the Delta core, the additional mmf that produces this voltage transformation is sourced directly from another phase limb. For example, phase A can exchange energy directly with phase B and phase C. This means that any transfer of energy will proportionally impact the phase the energy has been transferred from. The Delta core arrangement allows the voltage to be controlled and balanced for all three phases simultaneously.

In the case of the Star core, the additional mmf that produces this voltage transformation is sourced from or provided to the central limb of the core which has the full magnetic energy of all three phases passing through it at all times. When a voltage control action is taken as described above, the resultant change in the phase being controlled is independent of the other phases. One explanation is that magnetic energy for each phase only flows through the related limb and the central limb, for example phase A magnetic energy will only flow through limb 30A and 30D.

Another possible explanation is that the equal and opposite reaction from the mmf change through the transfer star being evenly divided between all three phases through the central core.

As an example, if phase A requires a voltage change, additional mmf can be injected into limb A through the transfer star which will result in a change in the $N_1:N_2$ for phase A. The mmf that created that change is sourced from the central limb of the core, meaning that all three phases (A, B, and C) are all equally effected by an amount equal to one third of the energy moved through the transfer star.

This ability to control voltage for a single phase without adversely impacting the balance of energy between the other phases is unique to this geometry. It allows the device to control both the root mean square (RMS) voltage of the 3 phase output of the device, as well as the instantaneous and RMS voltage of each phase independently. This functionality allows both independent phase voltage control and harmonics suppression.

Power Factor Control

Figure 15:
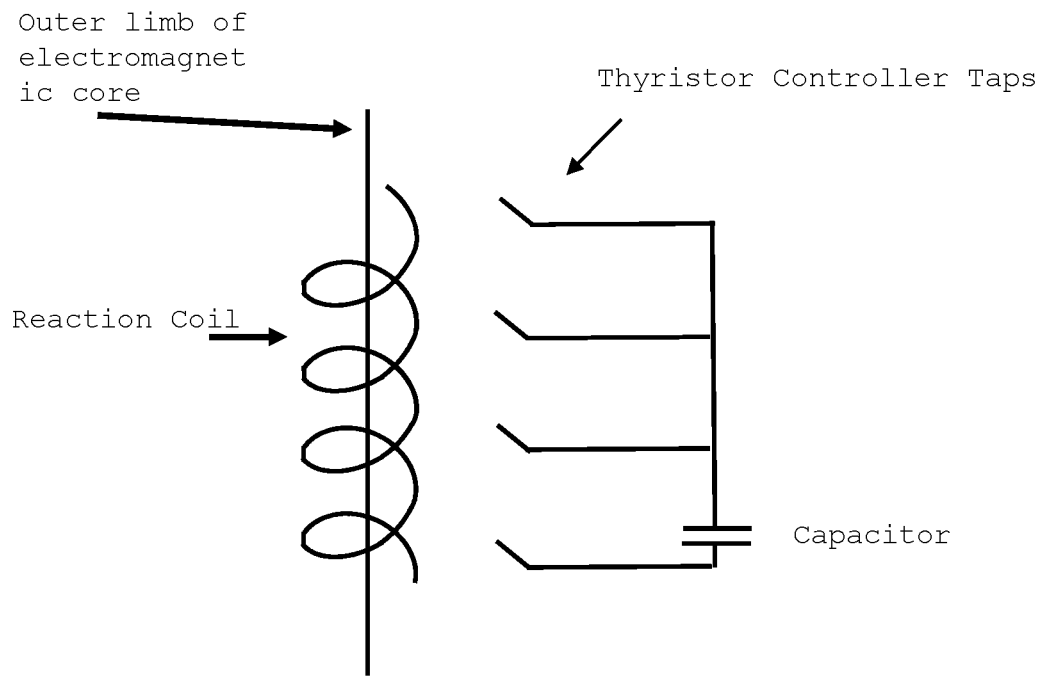
FIG. 15 is a representation of a coil with thyristor controlled taps to change the reactance of the reaction coil.

The magnetic core 100 has 6 reaction coils, denoted as 24U, 24L (Delta core) and the magnetic core 101 has 6 reaction coils, denoted as 44U, 44L (Star core), wound concentrically with the upper and lower coils on each of the three phases. The reaction coils are connected to capacitors via thyristor-controlled taps to regulate the discrete levels of reactive power injection or extraction as shown in FIG. 15.

Figure 16:
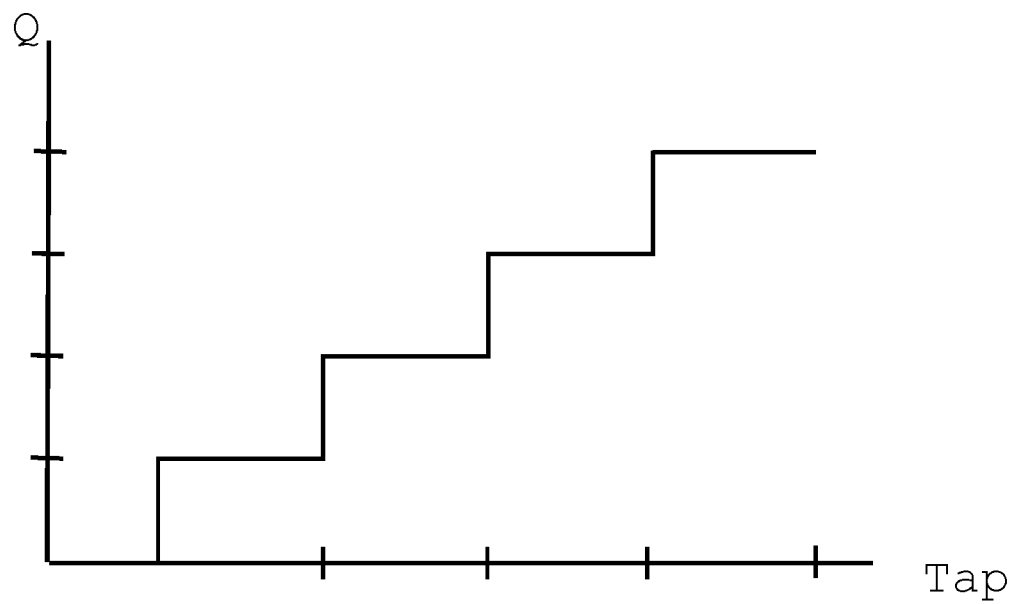
FIG. 16 is a graph of the relationship between the reactance and the tap position of the reaction coil.

Changing the tap position via the thyristors changes the reactance of the reaction coil as shown in FIG. 16, and therefore the impedance of the circuit. This allows the input power factor to be held at the desired level (usually unity) despite large real and reactive power variations of the load. Fine adjustment of the input power factor can be accomplished by injecting reactive power through either the reaction or transfer coils as required.

Control Methodology

Figure 5:
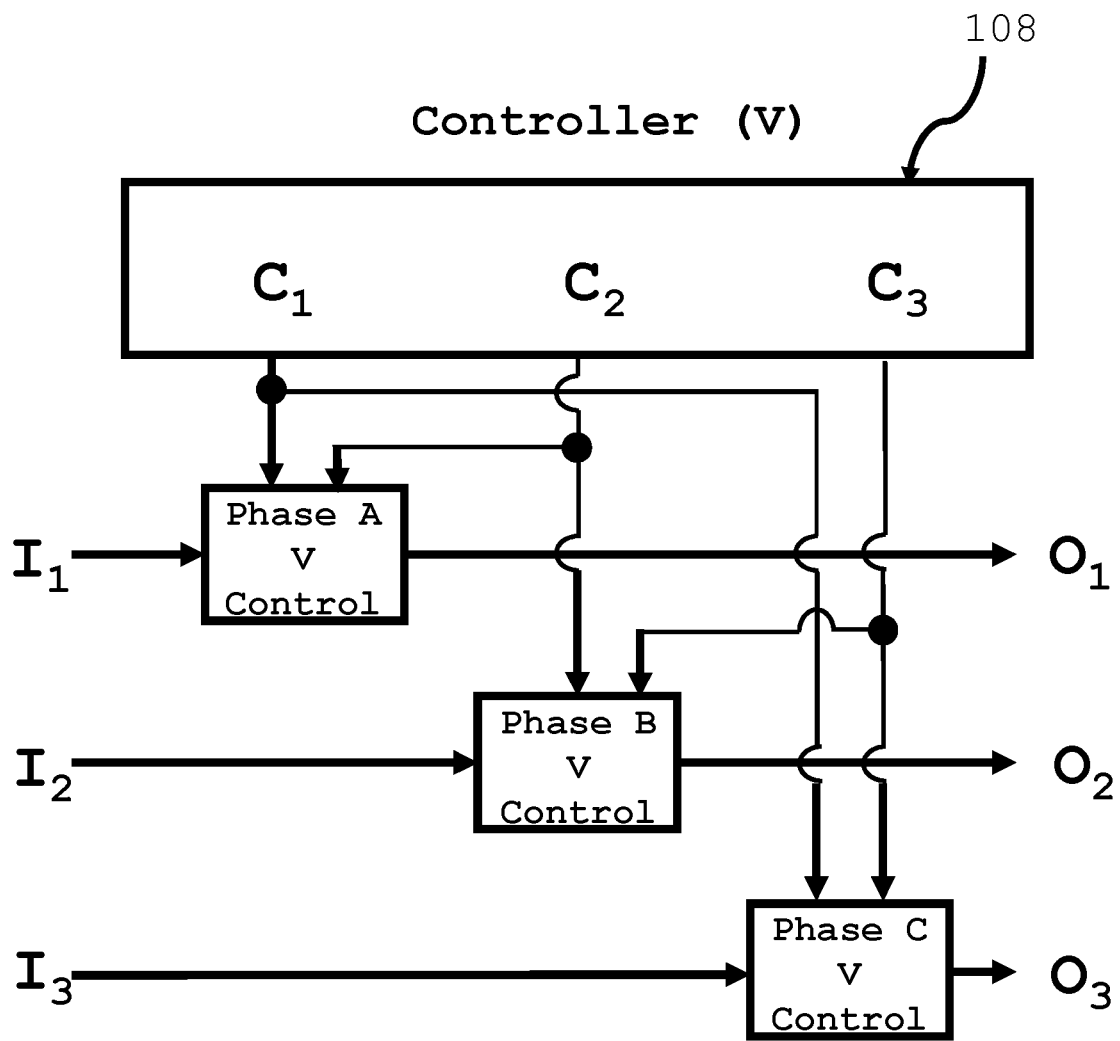
FIG. 5 is a block diagram of the voltage control system and process in accordance with some embodiments of the present invention.

For the Delta core, as all three phases within the device are symmetrically connected, the flux flowing generated in phase A will flow evenly between phases B and C to complete the circuit. This is true of all three phases. This results in a change to any phase having an impact on the other two. Each transfer coil is connected to two of the phase limbs, for example in FIG. 3, transfer coil $T_{AC}$ is connected directly to phase A and C. Therefore the control of $T_{AC}$ will impact the voltage control of phase A and or phase C depending on the point in the AC power cycle. Controller 108 provides a separate control signal for each transfer coil to produce the desired voltage control of the output as shown in FIG. 5.

Figure 29:
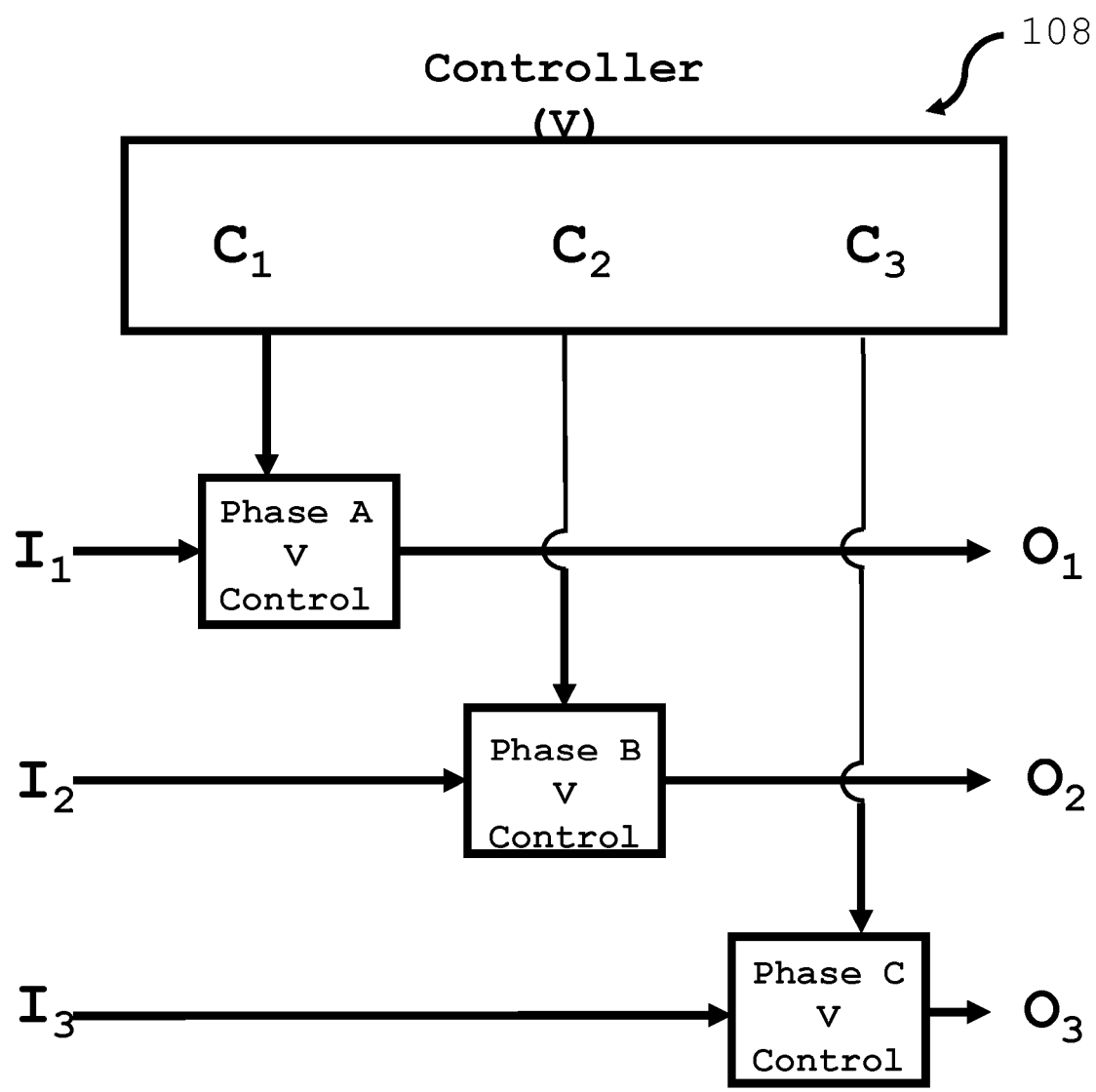
FIG. 29 is a block diagram of the voltage control system and process in accordance with some embodiments of the present invention.

For the Star core each transfer coil is wound on one arm of the transfer star, connected between the central limb of the core and one of the outer phase limbs, for example in FIG. 28 where transfer coil $T_A$ is connected directly between the central limb 30D and Phase A limb 30A. Therefore, the control of $T_A$ will only impact the voltage control of phase A. A separate control signal may be provided for each transfer coil to produce the desired voltage control of the output as shown in FIG. 29. For example, in some embodiments controller 108 provides a separate control signal for each transfer coil to produce the desired voltage control of the output as shown in FIG. 29.

The IGBTs in the power electronics 104 shown in FIG. 17 for the Delta core and FIG. 32 for the Star core are switched on and off by the controller in order to provide the desired power level in the control coil using a PWM scheme. For example, in some embodiments, the controller 108 opens and closes the transistors using a pulse width modulation (PWM) scheme, where a waveform is approximately by opening and closing the gates with varying durations. PWM control methods can include simple boost, maximum boost, constant boost, direct torque, and modified space vector. In addition to using PWM, other control methodologies may be used to achieve the result of power flow control through the transfer coils without changing the scope of this invention. These control methodologies include but are not limited to open loop, closed loop, fuzzy control, sliding mode control, model predictive control, field-oriented control (also known as vector control).

This power level is determined by the controller in order for the correct amount of mmf to be transferred through the transfer ring 16 between phases in the delta core, or between the phase limb and central limb through the transfer star 36 in the star core. The higher the power level through the transfer coil, the higher the transferred mmf, and the higher the amount of voltage control between the primary and secondary on that phase. An example of the electrical connection between the power electronics 104 and the transfer coils is shown in FIG. 18 for the Delta core, and FIG. 33 for the star core.

The controller 102 receives information from sensors on the primary and secondary coils to determine the voltage and phase angle of the power waveform on the input and output of the device. The controller then compares the output waveform to the target or "desired" output waveform. Any difference between the actual and target outputs creates a delta signal and control 108 generates a corresponding control signal for the PWM control for the voltage control capabilities described herein.

Figure 21:
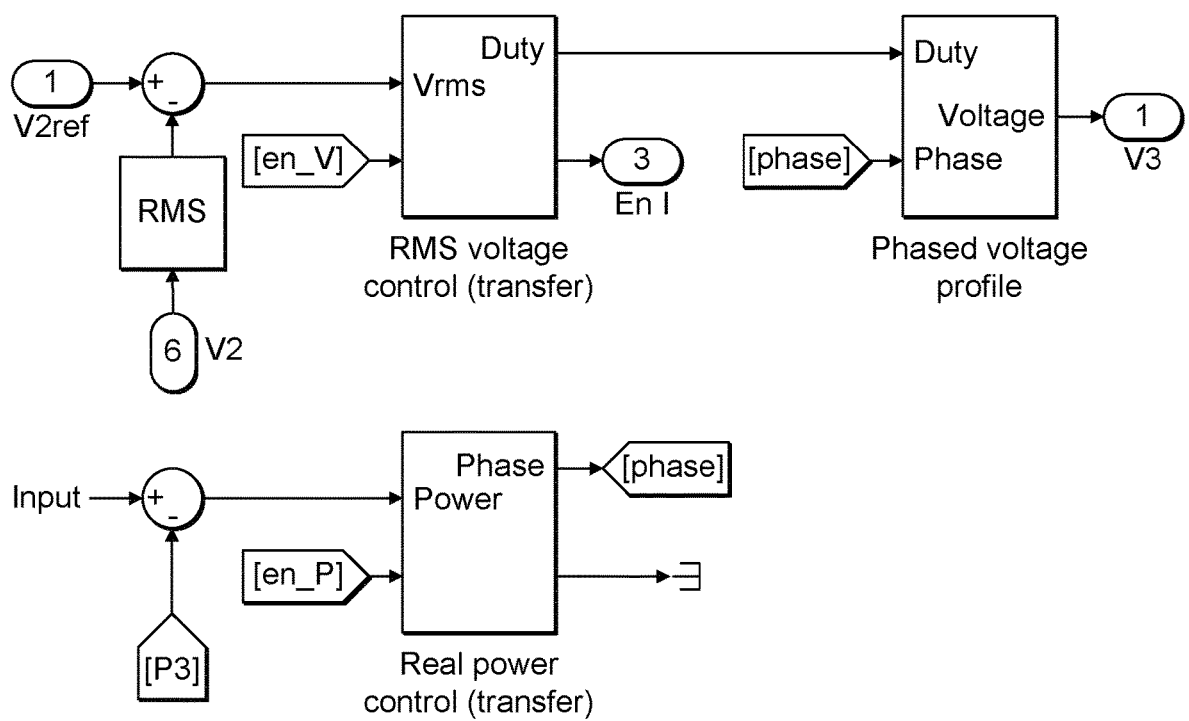
FIG. 21 is a software function block diagram showing component parts of the device control algorithms for voltage control.

One such implementation is shown in FIG. 21, as a high level function block control diagram for the voltage control 108. A reference RMS voltage is compared with the actual measured voltage. When voltage control is enabled, Vrms Control 502 generates a duty cycle and the real power control 506 generates a phase reference. These two parameters are then provided to the phased voltage profile generator 504, which provides the power electronics with the signals required to activate the transistor gates.

Figure 22:
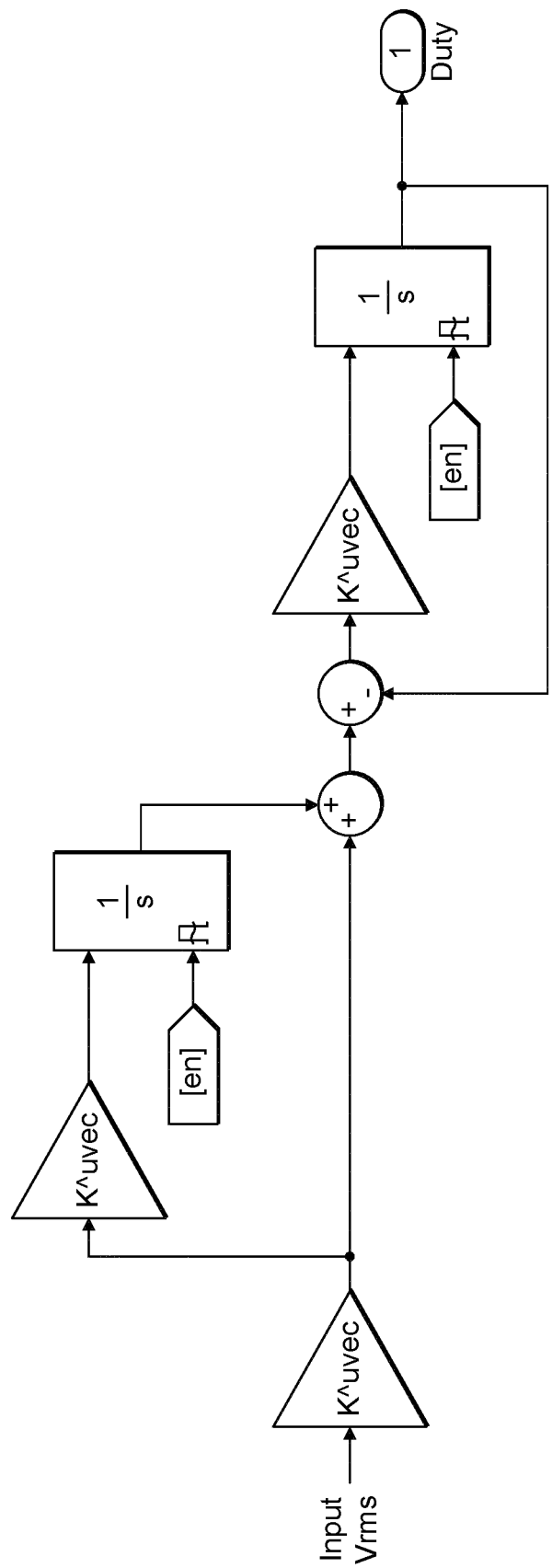
FIG. 22 is a software function block diagram showing a control strategy for voltage control in accordance with some embodiments of the present invention.

There are a number of ways Vrms Control 502 can be achieved, with one such implementation shown in FIG. 22. In this instance a PI (proportional-integral) control strategy is being used with a feedback loop to generate the duty cycle for a phase.

Figure 23:
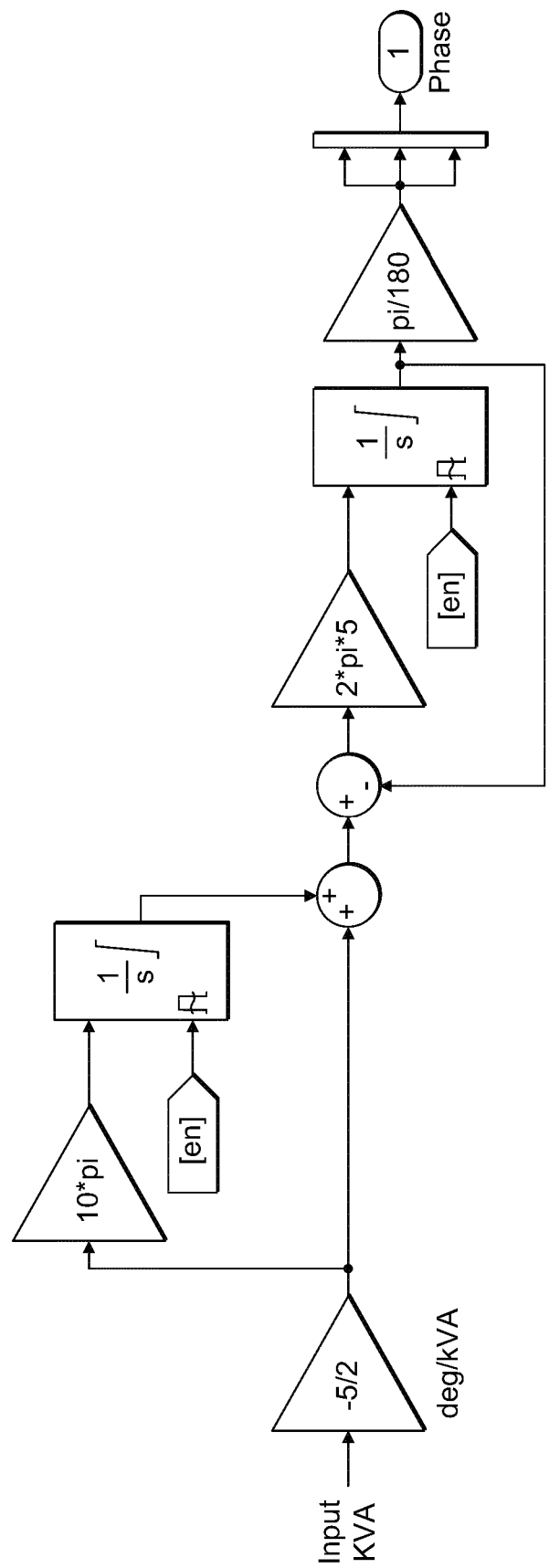
FIG. 23 is a software function block diagram showing a control strategy for real power control in accordance with some embodiments of the present invention.

There are a number of ways real power control 506 can be achieved, with one such implementation shown in FIG. 23. In this instance a PI (proportional-integral) control strategy is being used with a feedback loop to generate the phase reference for each phase.

Figure 24:
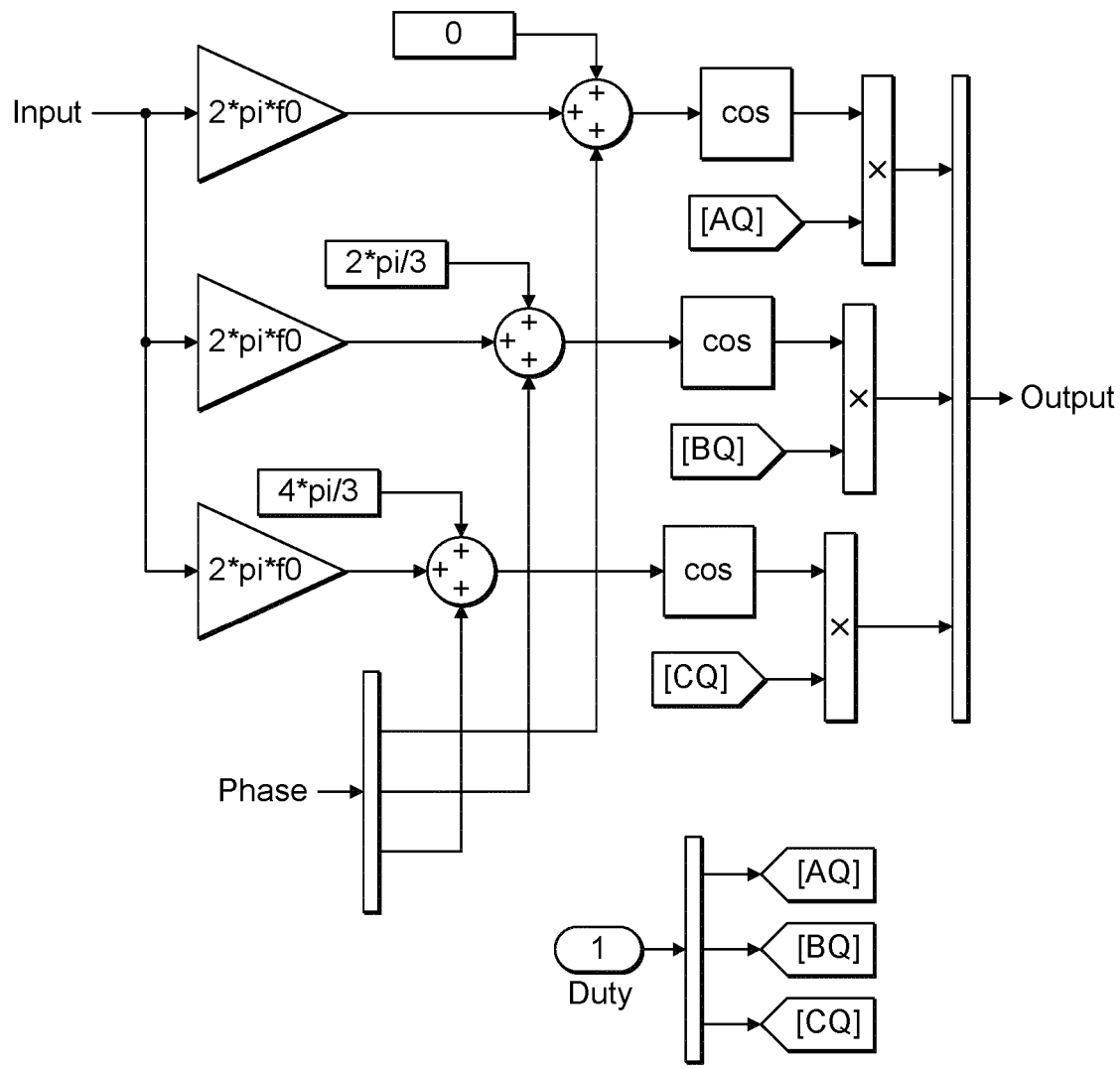
FIG. 24 is a software function block diagram showing a control strategy for generating a phase voltage profile in accordance with some embodiments of the present invention.

There are a number of ways phased voltage profile generator 504 can be achieved, with one such implementation shown in FIG. 24. The phase from the real power control 506 is the summed with the optimal phase angle separation of 120 degrees, and the measured phase angle. The cosine of each of these is combined with the duty component for each phase from the Vrms control 502. The output of this phased voltage profile generator 504 is the reference signal that controls the IGBT gates in FIG. 13, and FIG. 18 for the Delta core and FIG. 33 for the Star core.

As both the input and output are AC waveforms with a constantly changing voltage, the magnitude and direction of the power in the control coil will be determined to correctly sum with the power waveform of that phase of the device.

As an example, for the Delta core, if the voltage in the phase is positive and a voltage increase is to be provided on the secondary to meet the target output voltage, the control algorithm will control the PWM to generate a positive mmf into the phase from both other phases. If all the transfer coils are wound in the same clockwise direction, the two power levels in the transfer coils will be equal and opposite in direction. If the voltage in the phase is positive and a voltage decrease is to be provided on the secondary to meet the target output voltage, the control algorithm will control the PWM to generate a negative mmf from the phase into the other phases. If the voltage level in the phase is negative, the power levels in the transfer coils will be inverted.

As an example for the Star core, if the voltage in the phase is positive and a voltage increase is to be provided on the secondary to meet the target output voltage, the control algorithm will control the PWM to generate a positive mmf into the phase from the central limb. If the voltage in the phase is positive and a voltage decrease is to be provided on the secondary to meet the target output voltage, the control algorithm will control the PWM to generate a negative mmf from the phase into the central limb.

It will be obvious to those skilled in the art that many different variations on the PWM control algorithm, as well as control methodologies and algorithms can be used to achieve the same effect.

As there are 6 reaction coils, 6 separate control signals may be provided to control the tap positions of each coil.

Figure 6:
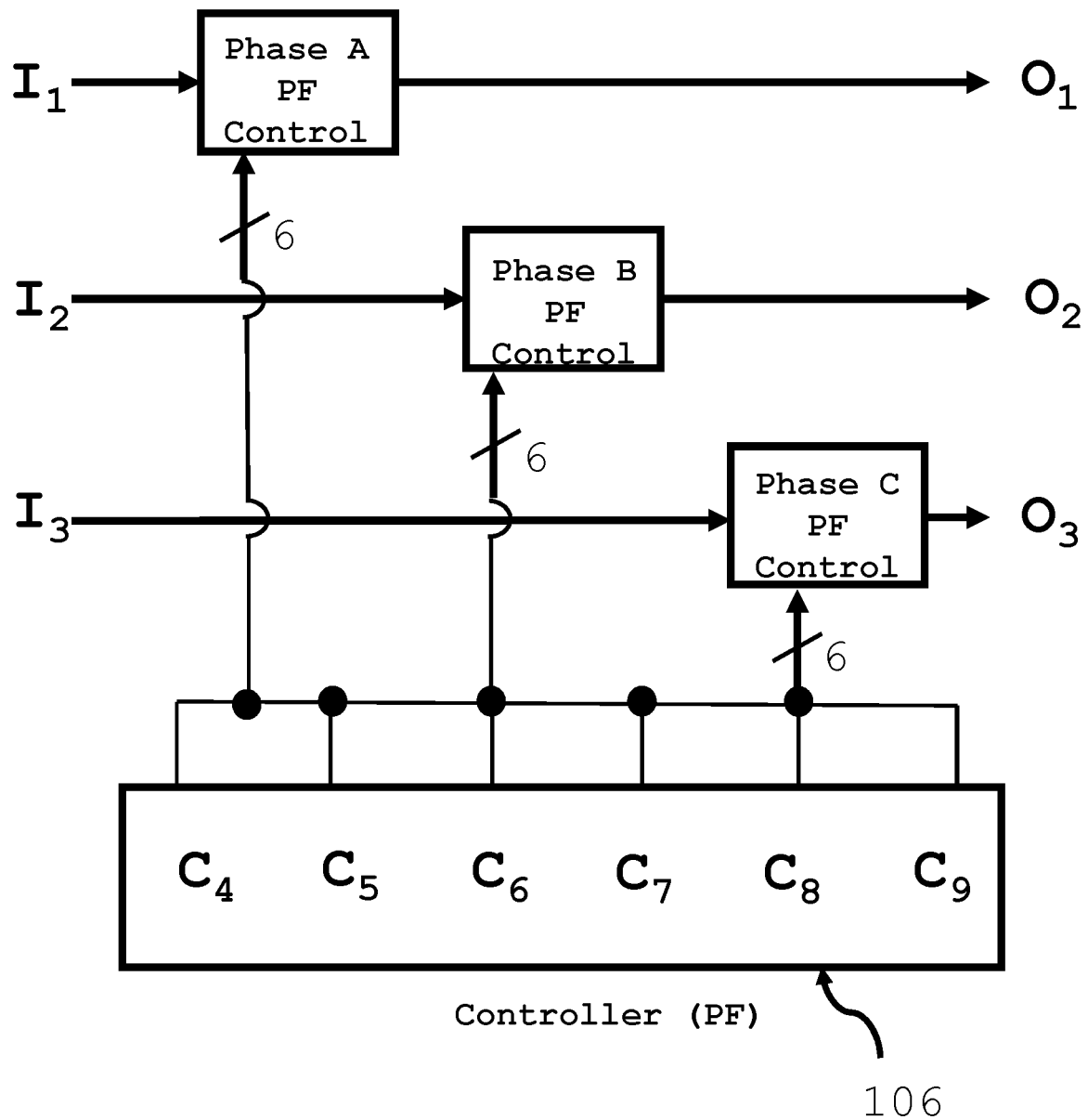
FIG. 6 is a block diagram of the power factor control system and process in accordance with some embodiments of the present invention.

For the Delta core all phases pass through all reaction coils, therefore the control 106 of these thyristors must consider the power factor control for all three phases as shown in FIG. 6.

Figure 30:
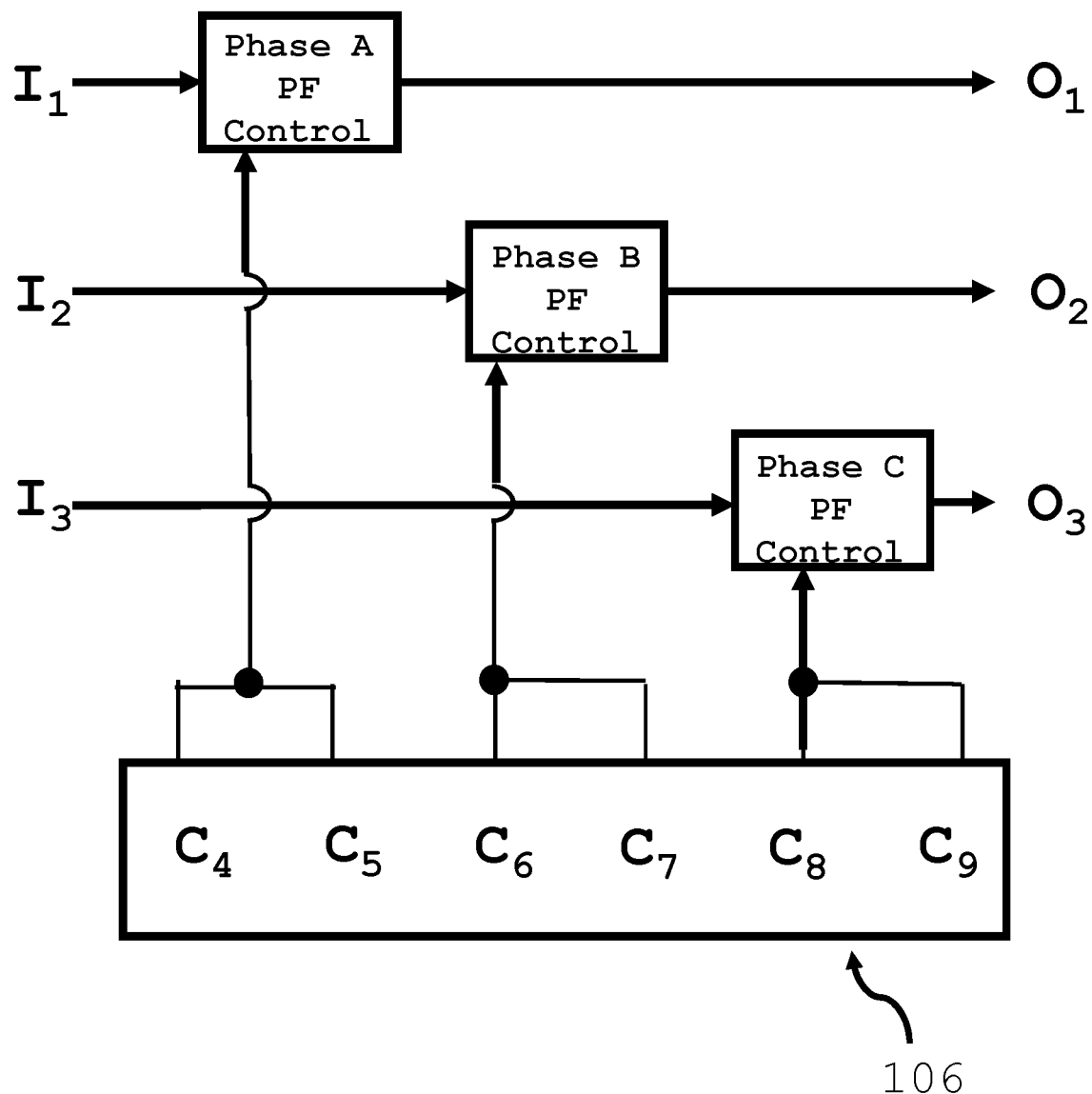
FIG. 30 is a block diagram of the power factor control system and process in accordance with some embodiments of the present invention.

For the Star core only a single phase passes through each of the reaction coils, therefore the control 106 of these thyristors need only consider the power factor control for that single phase as shown in FIG. 30.

Figure 25:
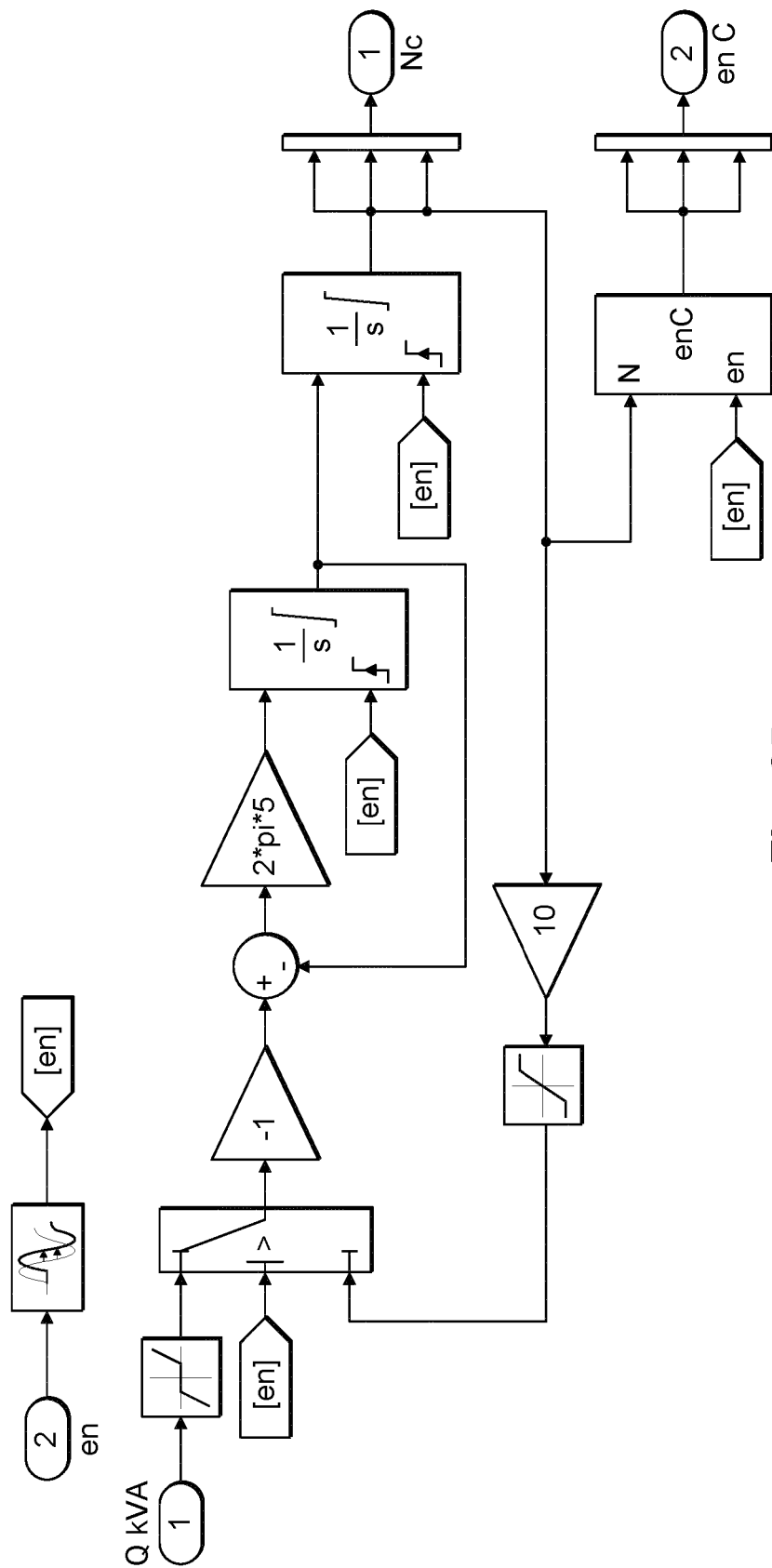
FIG. 25 is a software function block diagram showing a control strategy for power factor control in accordance with some embodiments of the present invention.
Figure 26:
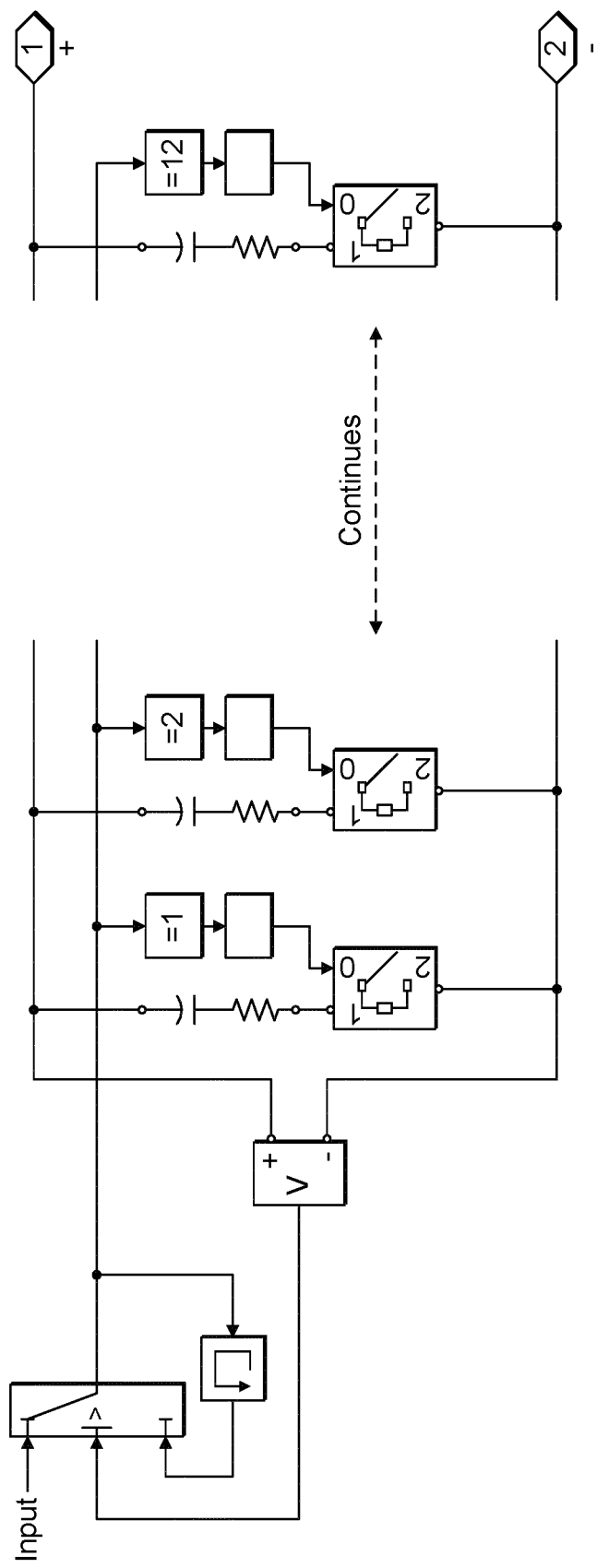
FIG. 26 is a software function block diagram showing a control strategy power electronic transistors to achieve power factor control in accordance with some embodiments of the present invention.

When a thyristor is activated, the tap position on the coil is changed which changes the number of turns connected in the circuit for that coil. This means that the impendence of the coil changes, and therefore the impedance of the magnetic circuit changes. This physical control provides an efficient way to change the impedance in larger discrete steps. One implementation to achieve power factor control 106 this is shown in FIG. 25. Nested integral control loops are used to determine the error between the reference and actual reactive power. This then outputs a tapping position number, relating to the physical tap position that should be used. This tap position number is used to activate the thyristors as shown for one of the three phases in FIG. 26.

Finer level of control around (up or down) these steps is possible by using the control coils to inject or extract reactive power. This is done by controlling the PWM of the transfer coils to phase shift the waveform in the coil. Having the control waveform out of phase with the flux in the core will result in the addition or subtraction of a reactive power component, depending on whether the transfer coil waveform is leading or lagging.

Single Phase Device

Figure 37:
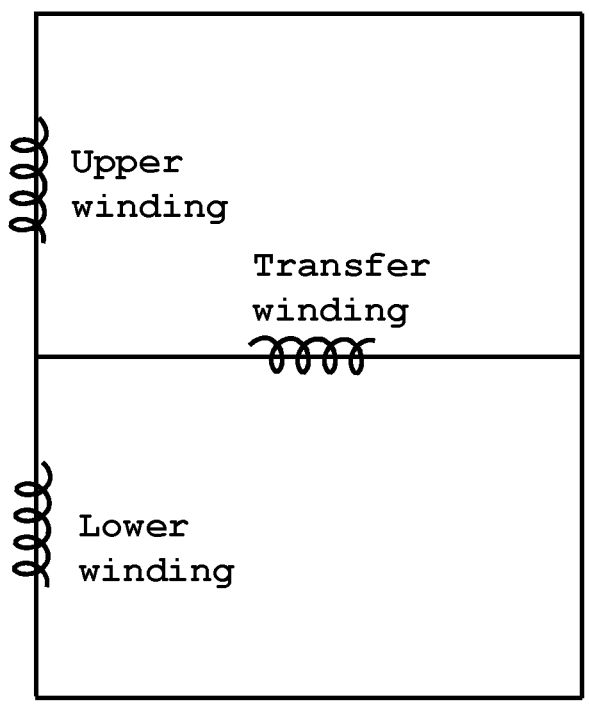
FIG. 37 is a two-dimensional single line representation of the electromagnetic core and windings from a single phase device in accordance with some embodiments of the present invention.

As described above, both the Delta core and Star core can be manufactured using the single phase core shown in FIG. 20. It is also possible to use a solitary single phase core of this shape and this winding arrangement to create a single phase transformer apparatus with the same voltage control, power factor control, and harmonic suppression capabilities as the three phase Star core. A single line representation of the electromagnetic core and windings is shown in FIG. 37.

Figure 38:
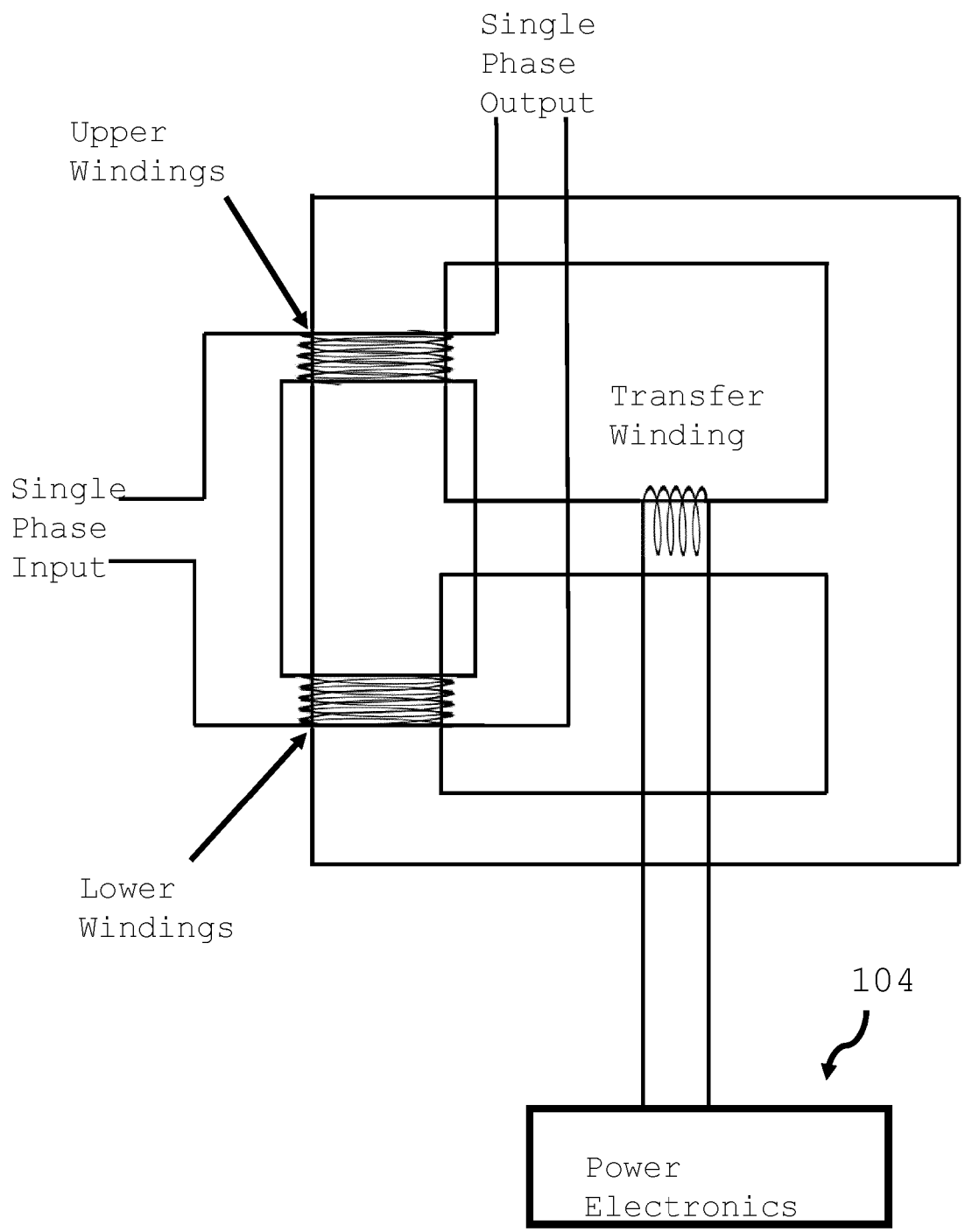
FIG. 38 is a diagram of a single phase electromagnetic core, with the primary and secondary coils connected to the electricity grid, and transfer coil connected to the power electronics.

The electromagnetic core and windings are connected to power electronics in order to achieve the power flow control capabilities described above as shown in FIG. 38, with a single phase shell type transformer core, a transfer winding on a transfer limb connected to power electronics 104, and concentrically wound primary and secondary windings connected in series above and below the transfer limb.

In some embodiments, reaction coils can also be concentrically wound with the upper and lower windings, connected to thyristor controlled taps as described above and shown in FIG. 15.

Figure 39:
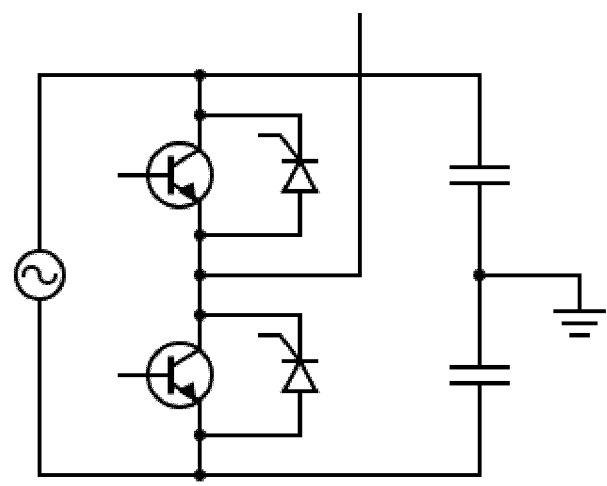
FIG. 39 is a circuit diagram of the power electronics approach to provide the pulse width modulation of the transfer coil for the single phase device.

The power electronics 104 to control the power flowing through the transfer winding can consist of a half bridge circuit as shown in FIG. 39. In some embodiments, the power electronics 104 may consist of a full H bridge circuit, or any other configuration to achieve the same ability to modulate power flow.

The control methodology and implementation for the single phase device is identical to one single phase of the 3 phase Star core system described above.

It will be apparent that the electrical power supply system and process described herein are particularly advantageous as they are able to dynamically and rapidly respond to changes in the input energy received by the system in order to generate corresponding output energy having a target voltage and a target input power factor. In particular, this ability allows the described system and process to match the output energy to the energy demanded by the loads on the system. Moreover, the system and process are bidirectional, meaning that they are able to do this for energy supplied from an energy grid and flowing in one direction, for example, and also for energy supplied from renewable energy sources, which may be flowing through the system in the opposite direction. For example, changes in local energy generation arising from changes in wind and/or changes in available sunlight are able to be mitigated by the system and process to provide a relatively constant output for a fixed load.

Many modifications will be apparent to those skilled in the art without departing from the scope of the present invention.

The invention claimed is:

1. A transformer apparatus for an electrical power transformation system comprising:
   three outer transformer limbs, each transformer limb comprising:
      an electromagnetic core;
      a first coil assembly comprising a first primary coil and a first secondary coil, the first primary coil and the first secondary coil wound concentrically around the electromagnetic core;
      a second coil assembly comprising a second primary coil and a second secondary coil, the second primary coil and the second secondary coil wound concentrically around the electromagnetic core;
      wherein the first coil assembly and the second coil assembly are spaced apart along the electromagnetic core,
      each first primary coil is connected in series to the second primary coil of the respective transformer limb, and
      each first secondary coil is connected in series to the second secondary coil of the respective transformer limb;
   an inner transformer limb comprising an electromagnetic core, wherein the outer transformer limbs are arranged about the inner transformer limb;
   a transfer star comprising:
      an electromagnetic transfer core extending from the inner transformer limb to each of the three outer transformer limbs at a point on each outer transformer limb between the first coil assembly and the second coil assembly;
      three transfer coils, the transfer coils wound around the electromagnetic transfer core such that each transfer coil is arranged between the inner transformer limb and a respective outer transformer limb,
      wherein the transfer star is configured to allow transfer of magnetomotive force between the outer transformer limbs and the inner transformer limb of the transformer apparatus;
   a first connecting portion provided towards a first end of each outer transformer limb and towards a first end of the inner transformer limb, the first connecting portion connecting each of the first ends of the outer transformer limbs and the first end of the inner transformer limb together and configured to allow magnetic flux to flow between each of the first ends of the inner and outer transformer limbs; and
   a second connecting portion provided towards a second opposing end of each outer transformer limb and towards a second opposing end of the inner transformer limb, the second connecting portion connecting each of the second ends of the outer transformer limbs and the second end of the inner transformer limb together and configured to allow magnetic flux to flow between each of the second ends of the inner and outer transformer limbs.

2. A transformer apparatus according to claim 1, wherein each first coil assembly further comprises:
   a first reaction coil wound concentrically around the electromagnetic core with the first primary coil and the first secondary coil; and
   each second coil assembly further comprises:
   a second reaction coil wound concentrically around the electromagnetic core with the second primary coil and the second secondary coil.

3. A transformer apparatus according to claim 1, wherein at least one of the transfer star, the first connecting portion, and the second connecting portion comprises a stacked laminate of an electromagnetic material.

4. A transformer apparatus according to claim 1,
   for each first coil assembly, the first secondary coil is wound around the electromagnetic core, and the first primary coil is wound concentrically around the first secondary coil; and/or
   for each second coil assembly, the second secondary coil is wound around the electromagnetic core, and the second primary coil is wound concentrically around the second secondary coil.

5. A transformer apparatus according to claim 2, wherein
   for each first coil assembly, the first reaction coil is wound around the electromagnetic core, and the first secondary coil is wound concentrically around the first reaction coil, and the first primary coil is wound concentrically around the first secondary coil; and/or
   for each second coil assembly, the second reaction coil is wound around the electromagnetic core, and the second secondary coil is wound concentrically around the second reaction coil, and the second primary coil is wound concentrically around the second secondary coil.

6. A transformer apparatus according to claim 1, wherein the electromagnetic core of each outer transformer limb comprises:
   a first electromagnetic core portion on which the first coil assembly is provided; and
   a second electromagnetic core portion on which the second coil assembly is provided,
   wherein the transfer star is provided between the first and second electromagnetic core portions of each outer transformer limb; wherein optionally the electromagnetic core of the inner transformer limb comprises:
   a first electromagnetic core portion; and
   a second electromagnetic core portion;
   wherein the transfer star is provided between the first and second electromagnetic core portions of the inner transformer limb.

7. A transformer apparatus according to claim 2, wherein each reaction coil has a variable reactance.

8. A transformer apparatus according to claim 1, wherein the inner transformer limb is arranged at a geometric centre of the outer transformer limbs.

9. A transformer apparatus according to claim 1, wherein the outer transformer limbs are arranged about the inner transformer limb 120° apart.

10. An electrical power transformation system configured to receive a three phase power input and output a three phase power output having a transformed voltage, the electrical power transformation system comprising:
- a transformer apparatus according to claim 1, wherein the first and second primary coils of each outer transformer limb are configured to be connected across a respective phase of the three phase power input, and the first and second secondary coils of each outer transformer limb are configured to be connected across a respective phase of the three phase power output;
- a controller configured to control each of the three transfer coils in order to selectively transfer magnetomotive force between the transformer limbs of the transformer apparatus based on the three phase power input and the three phase power output.

11. An electrical power transformation system according to claim 10, wherein each first coil assembly of the transformer apparatus further comprises:
- a first reaction coil wound concentrically around the electromagnetic core with the first primary coil and the first secondary coil; and
- each second coil assembly of the transformer apparatus further comprises:
- a second reaction coil wound concentrically around the electromagnetic core with the second primary coil and the second secondary coil,
- wherein the controller is further configured to:
- determine a power factor of the three phase power output on the secondary coils and output a reaction signal to each reaction coil to control a reactance of the respective reaction coil in order to control a power factor of the three phase power input on the primary coils.

12. An electrical power transformation system according to claim 11, wherein each reaction coil has a variable, wherein the electrical power transformation system further comprises:
- a plurality of reaction circuits, each reaction circuit configured to control the variable reactance of a respective reaction coil in response to a respective reaction signal from the controller.

13. An electrical power transformation system according to claim 12, wherein the controller outputs a reaction signal for each reaction circuit to control the variable reactance of the respective reaction coil in order to control a power factor of the three phase power input.

14. An electrical power transformation system according to claim 10, wherein
- the controller controls each of the three transfer coils in order to selectively transfer magnetomotive force between the inner and outer transformer limbs of the transformer apparatus in order to control a ratio of voltage transformation between the primary and secondary coils of each outer transformer limb.

15. An electrical power transformation system according to claim 10, further comprising:
- an inverter circuit configured to drive each of the three transfer coils in response to a control signal from the controller.

16. An electrical power transformation system according to claim 15, wherein the inverter circuit further comprises:
- at least one energy storage element for each of the three transfer coils configured to store energy for driving each of the three transfer coils.

17. An electrical power transformation system transformer apparatus according to claim 15, wherein the inverter circuit outputs a pulse width modulated signal to each of the three transfer coils.

18. An electrical power transformation system according to claim 15, wherein the controller is configured to:
- control a phase of a control signal driving each transfer coil with respect to a phase of the three phase input power to control a reactive power transferred between transformer limbs of transformer apparatus.

19. A method of transforming three phase power comprising:
- inputting a three phase power input to the electrical power transformation system of the transformer apparatus of claim 10;
- transforming the three phase power input to a three phase power output, wherein a voltage and/or power factor of the three phase voltage output is controlled by the controller.

\* \* \* \* \*